United States Patent [19]

Evans-Paganelli et al.

[11] Patent Number: 5,265,010

[45] Date of Patent: Nov. 23, 1993

[54] METHOD AND APPARATUS FOR PERFORMING PATIENT DOCUMENTATION

[75] Inventors: Barbara Evans-Paganelli, Reading; Maria Hendrickson, Chelmsford, both of Mass.

[73] Assignee: Hewlett-Packard Company, Palo Alto, Calif.

[21] Appl. No.: 523,732

[22] Filed: May 15, 1990

[51] Int. Cl.$^5$ .................. G06F 15/42; G06F 15/74
[52] U.S. Cl. .......................... 364/413.02; 364/413.01
[58] Field of Search ................... 364/413.01, 413.02; 395/155, 156, 157, 161

[56] References Cited

U.S. PATENT DOCUMENTS

| | | | |
|---|---|---|---|
| 4,130,881 | 12/1978 | Haessler et al. | 364/413.02 |
| 4,290,114 | 9/1981 | Sinay | 364/413.02 |
| 5,065,315 | 11/1991 | Garcia | 364/413.02 |

OTHER PUBLICATIONS

"An Automated Kardex and Care Plan", Irene Hinson, Nettie Silva, and Pat Clapp, Nursing Management, Jul. 1984, pp. 35, 36, 38–42.

Huei-Ning et al, "An Interactive System for Generating Hospital Progress Notes", pp. 378–384, Oct. 1989.

Naeymi-Rad, F. et al, "Maintaining a Knowledge Base Using the Medas Knowledge Engineering Tools", pp. 298–303, 1985.

Cushing, M., Jr. "Humabase", pp. 110–113, 1990.

Warshawsky, S. "Primary Care Medical Records: A Proposed Structure to Encourage Their Use", pp. 131–133, 1991.

Asimacopoulos A. et al. "An Electronic Notebook for Problem-Oriented Patient Progress Notes", pp. 813–817, Oct. 1989.

*Primary Examiner*—Roy N. Envall, Jr.
*Assistant Examiner*—Jennifer L. Hazard

[57] ABSTRACT

This invention provides a hospital patient documentation method and apparatus which is used to generate an initial patient health plan which identifies the patient's health problems, the causes of the problems, expected outcomes, and interventions to achieve such outcomes. The system also provides for the periodic entry of progress notes on the patient, with the system automatically updating the care plan for the patient in response to the progress notes. The initial care plan and all updates are stored so that a audit trail is maintained and the user may obtain either a current patient health plan or a historical patient health plan on demand. The system is menu driven to facilitate uniformity and menu items are coded to facilitate subsequent retrieval and processing. Outcomes are displayed with outcome due dates and progress note generation may be inhibited if, on an outcome due date, the outcome has not been achieved or the due date updated.

65 Claims, 38 Drawing Sheets

```
┌──────────────┬─────────────────────────────────────────────────────┬──────┐
│              │ 3 ICU WESTWATSON, LULU MRN #123-45678 DX: S/P CABG x4│  ?   │
├──────────┬───┴───────┬─────────┬────────┬──────┬──────┬────────────┤  o   │
│MAIN MENU │DATA ENTRY │OPTIONS  │ PRINT  │      │      │            │HELP  │
└──────────┴───────────┴─────────┴────────┴──────┴──────┴────────────┴──────┘
```

| INDIVIDUAL PROBLEMS/DIAGNOSIS SELECT FROM ALPHABETICAL LIST | STANDARD CARE PLANS SELECT BODY SYSTEM TO INDEX CARE PLAN |
|---|---|
| A-B | CARDIOVASCULAR |
| C-D | NEUROLOGIC / NEUROSURGICAL |
| E-G | RESPIRATORY |
| H-K | GASTROINTESTINAL |
| L-P | GENITOURINARY |
| Q-S | ENDOCRINE / METABOLIC |
| T-Z | INTEGUMENTARY / MUSCULOSKELETAL |
| CANCEL | HEMATOLOGIC |
|  | EENT |
|  | PYSCHO / SOCIAL |
|  | CANCEL |

| SYSTEM MESSAGE AREA | TUES 10 JAN 89 5:45pm |
|---|---|

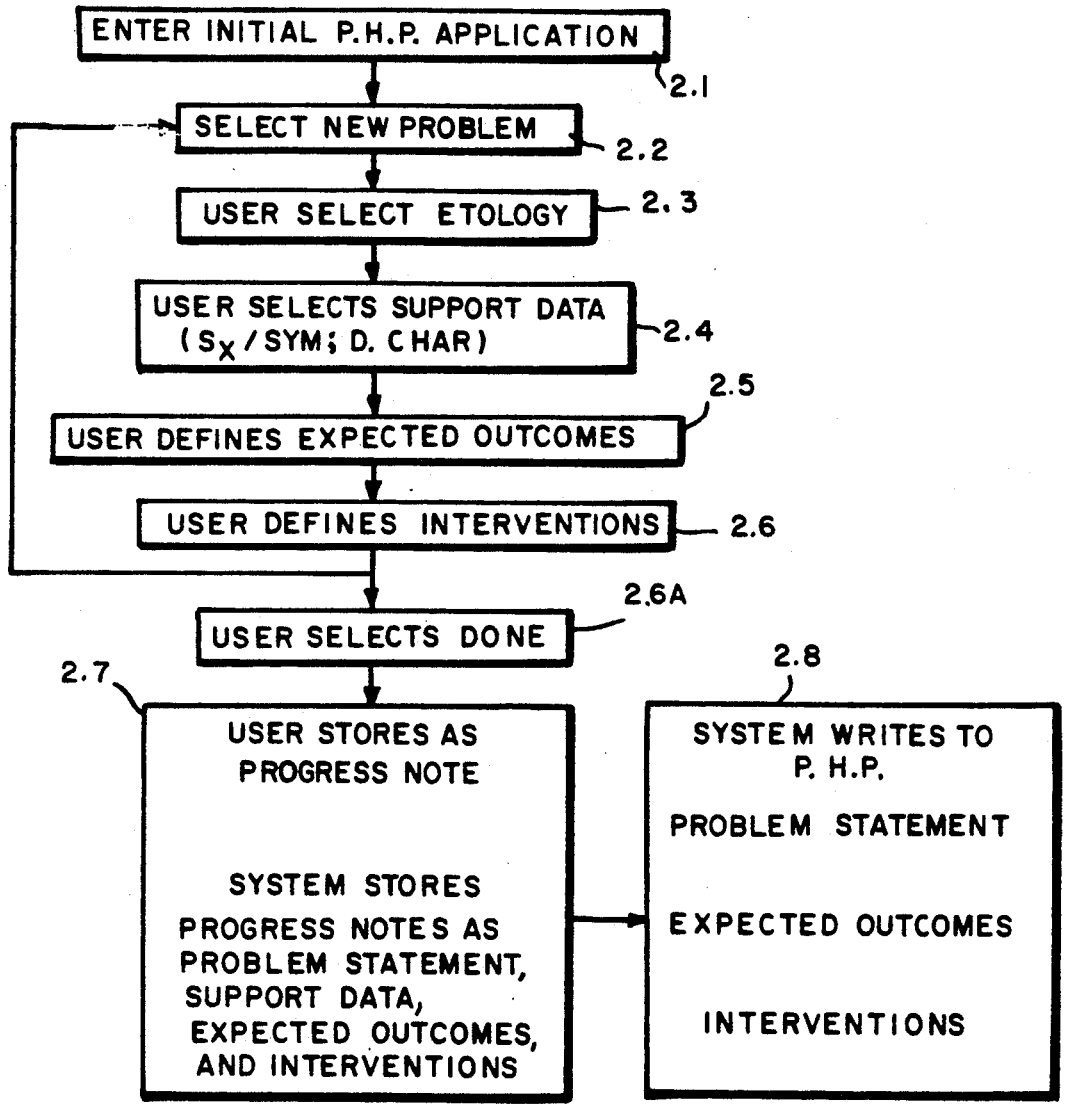
FIG. 2.0
FIG. 2.1

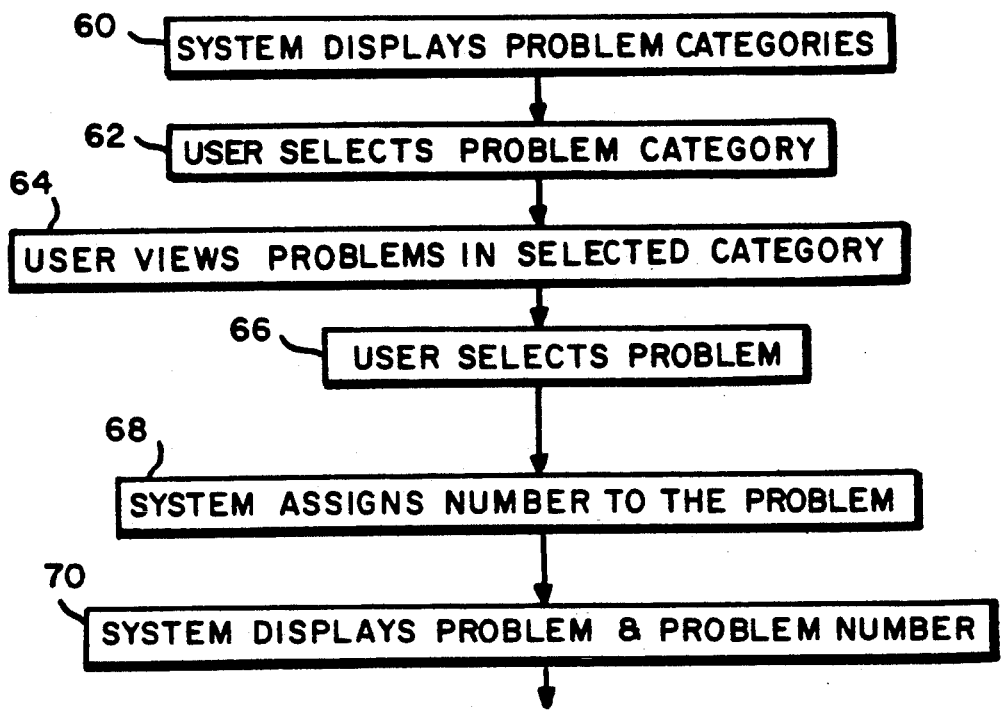
FIG. 2.2
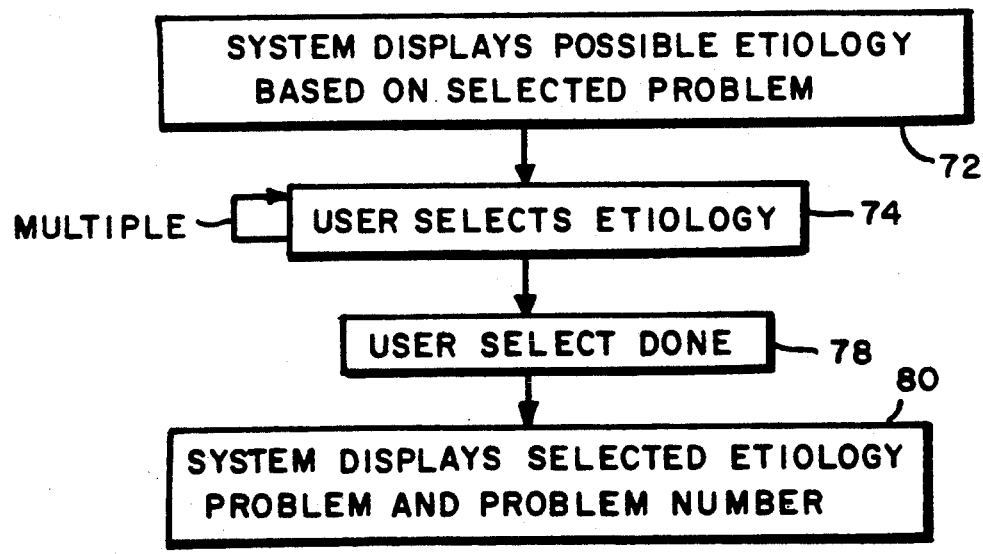
FIG. 2.3

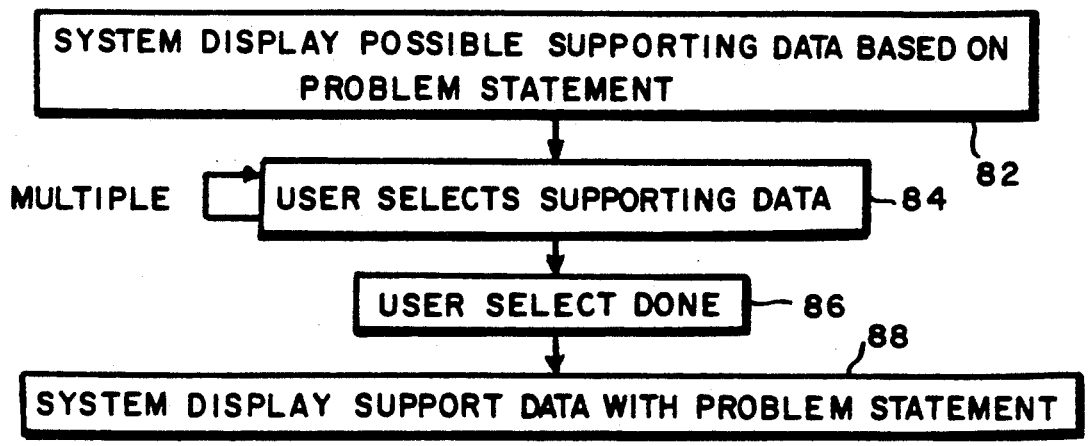
FIG. 2.4
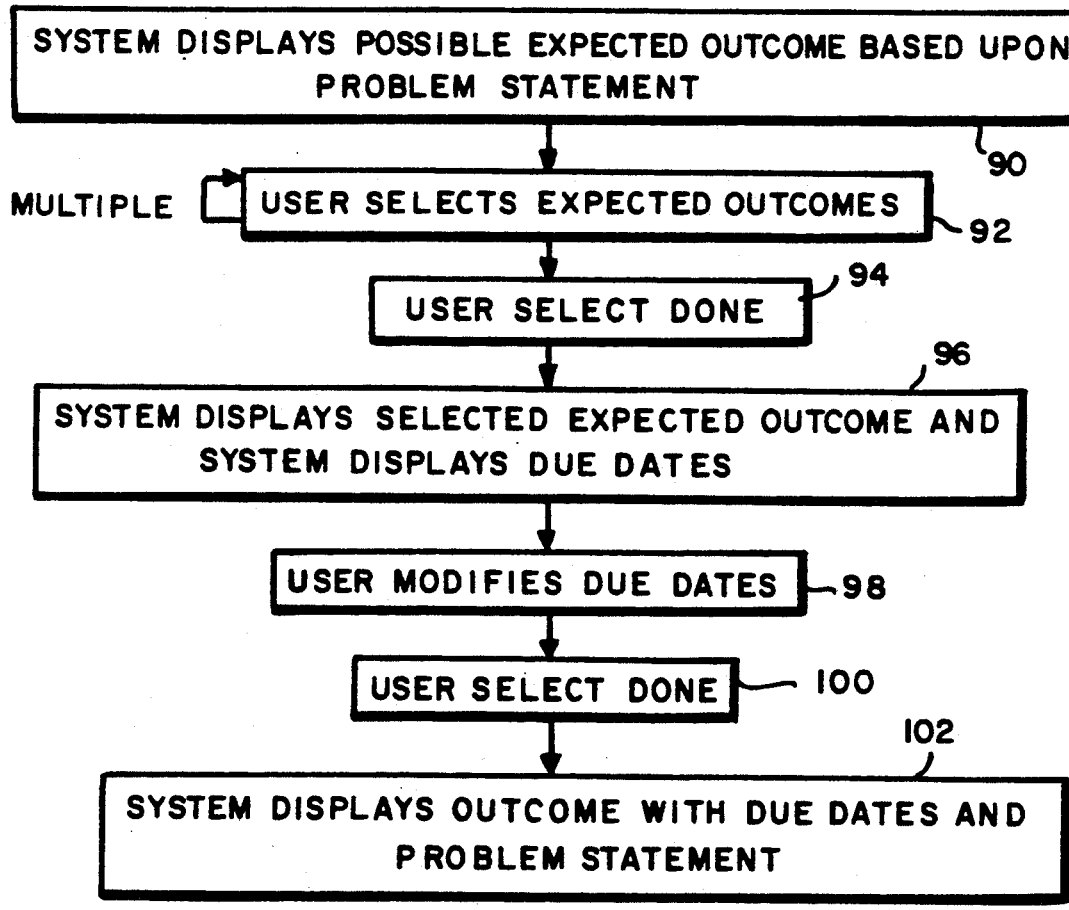
FIG. 2.5

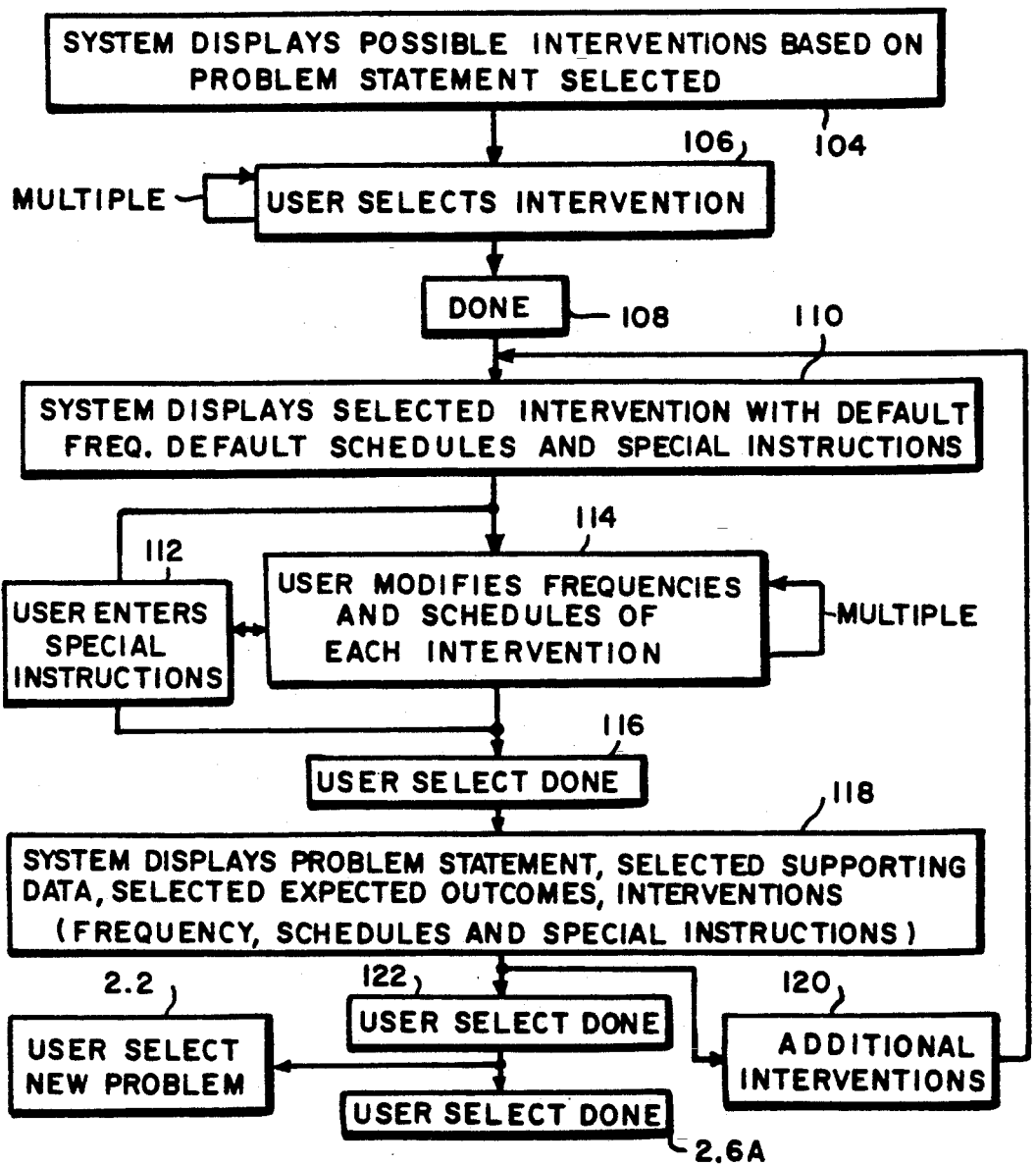
FIG. 2.6
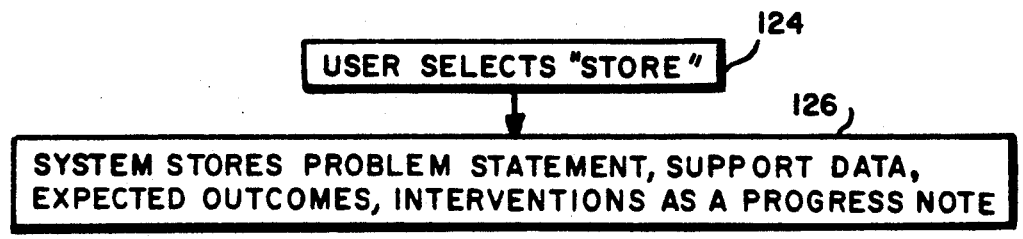
FIG. 2.7

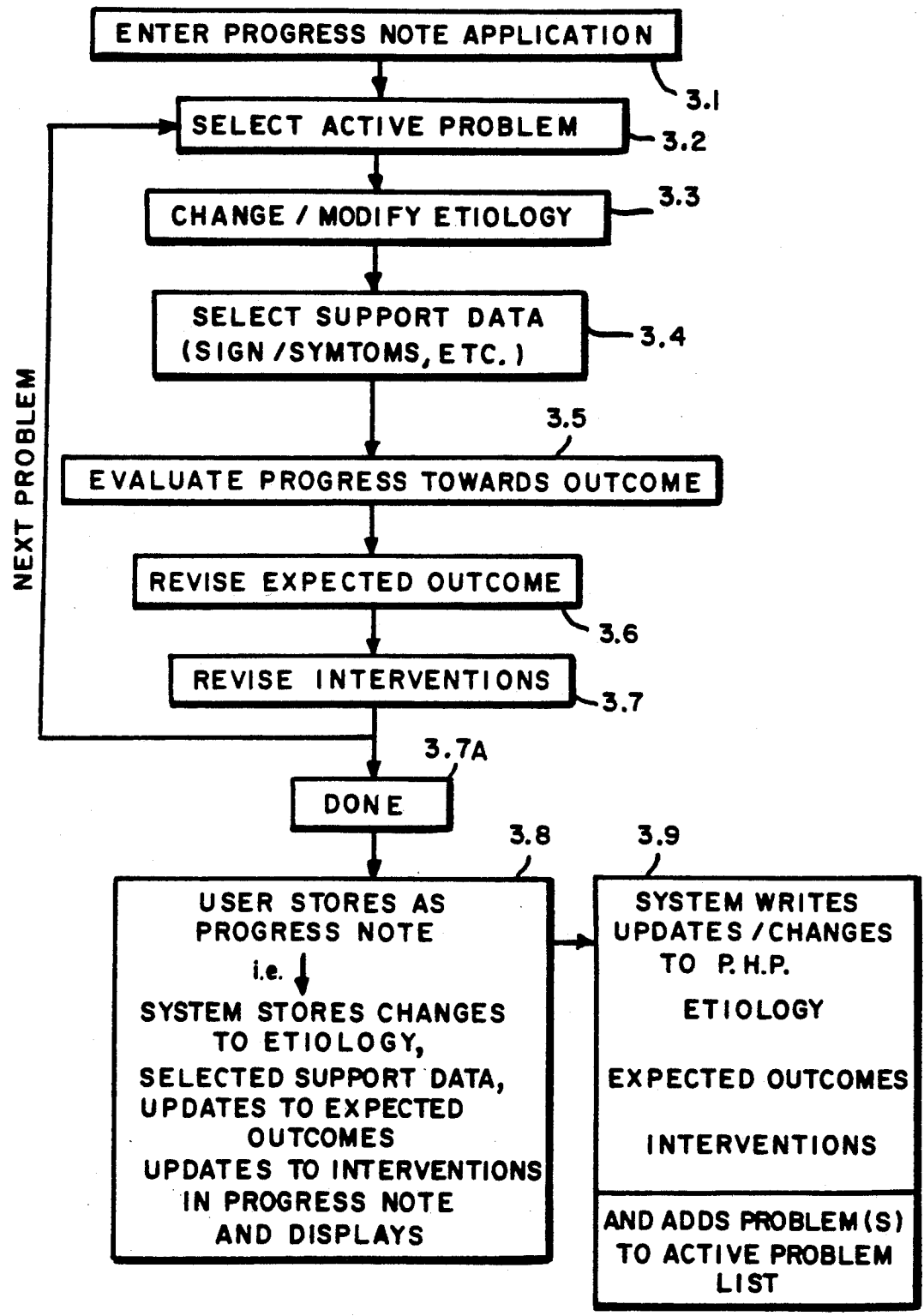
FIG. 3.0

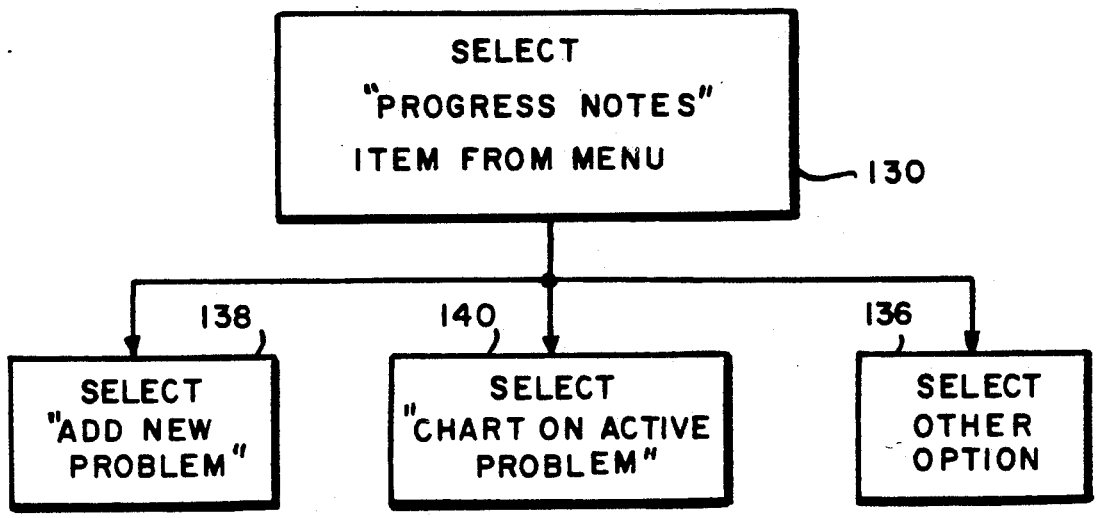
FIG. 3.1
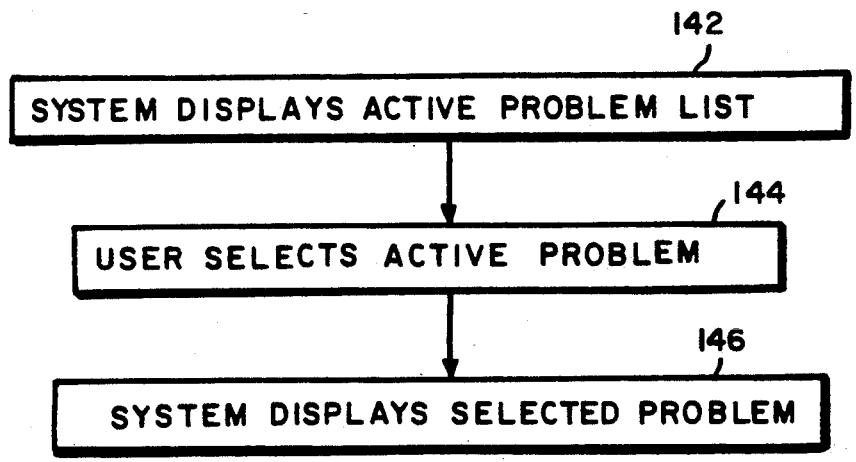
FIG. 3.2

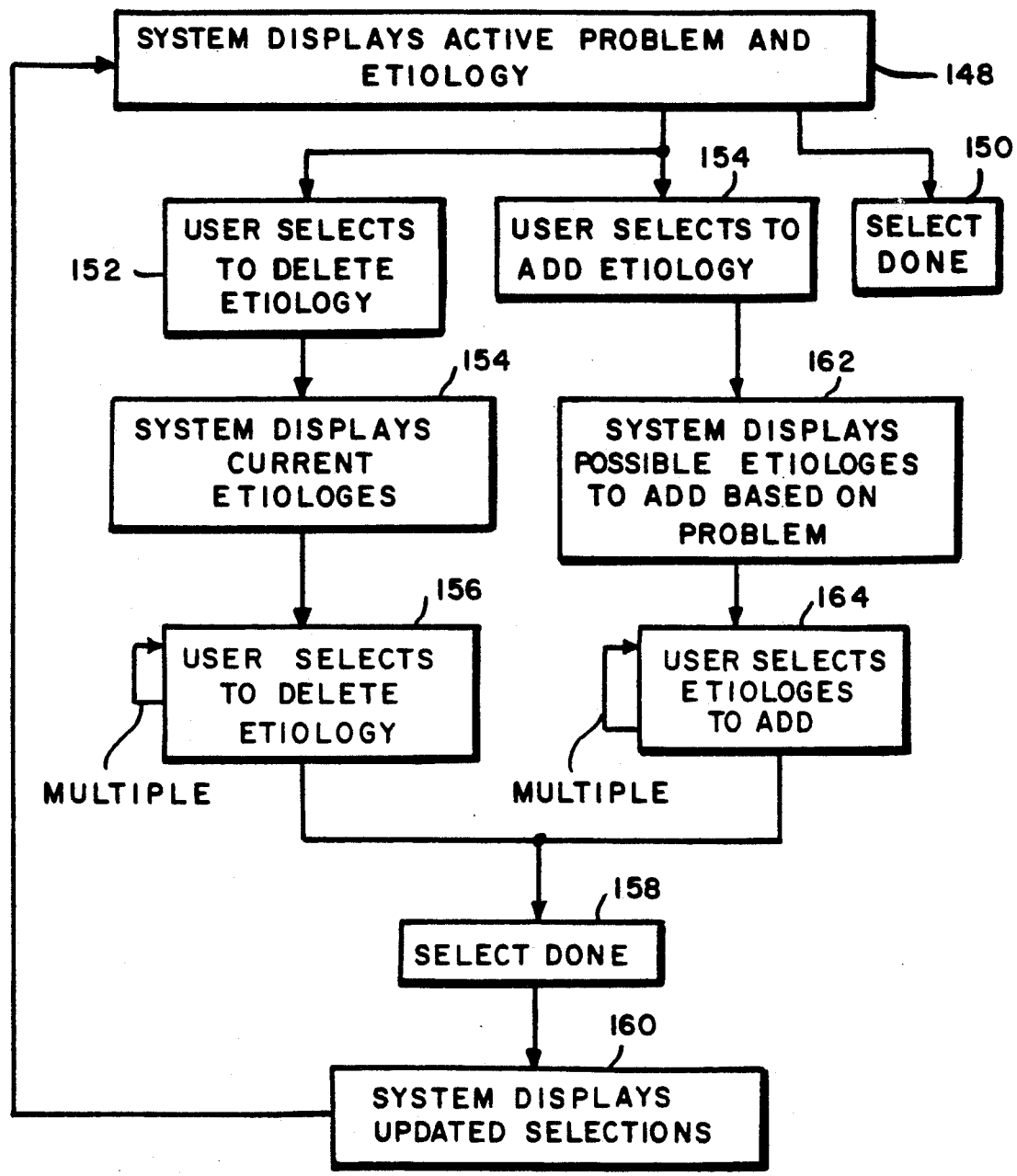
FIG. 3.3

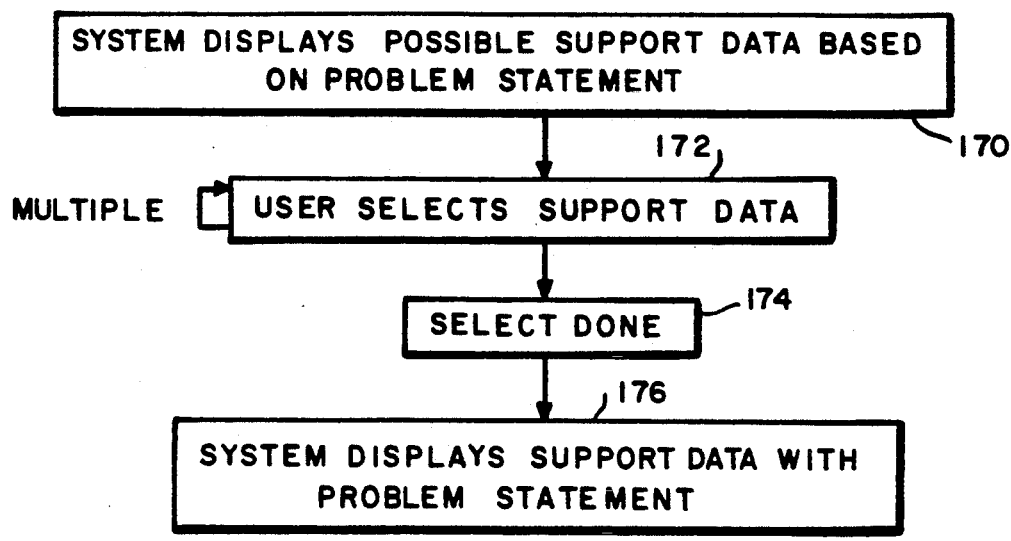
FIG. 3.4
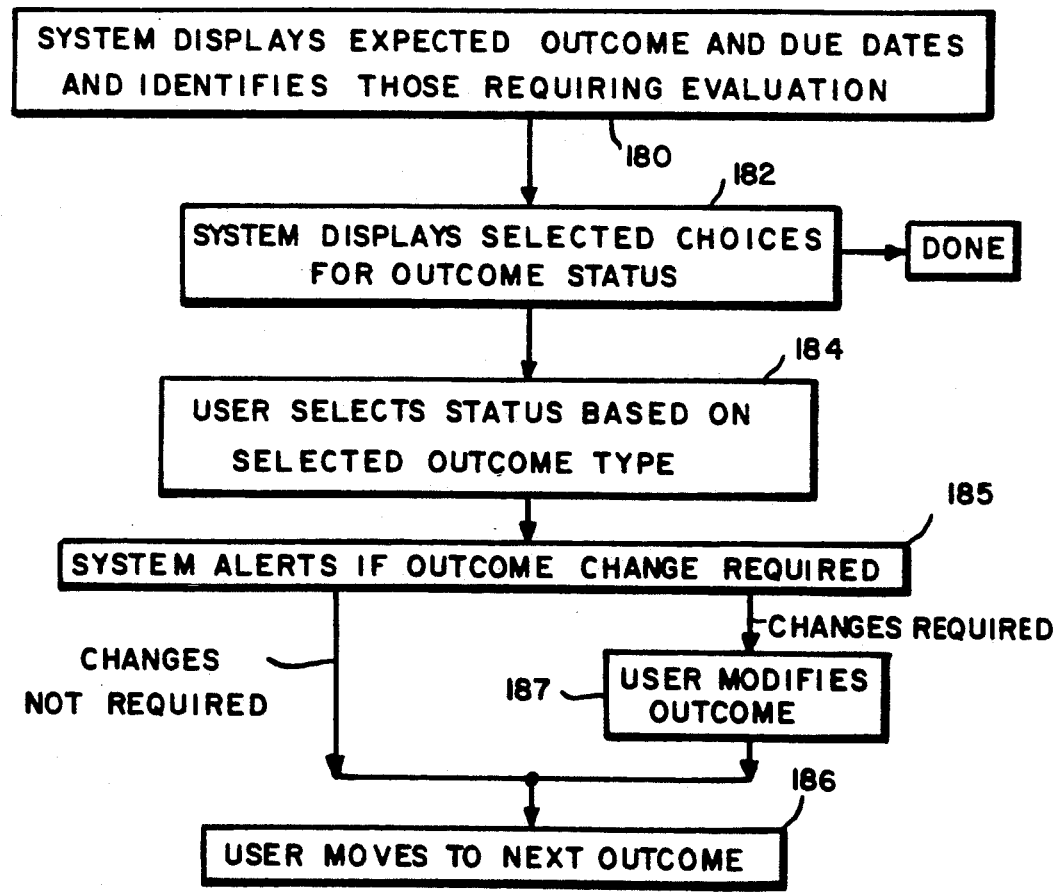
FIG. 3.5

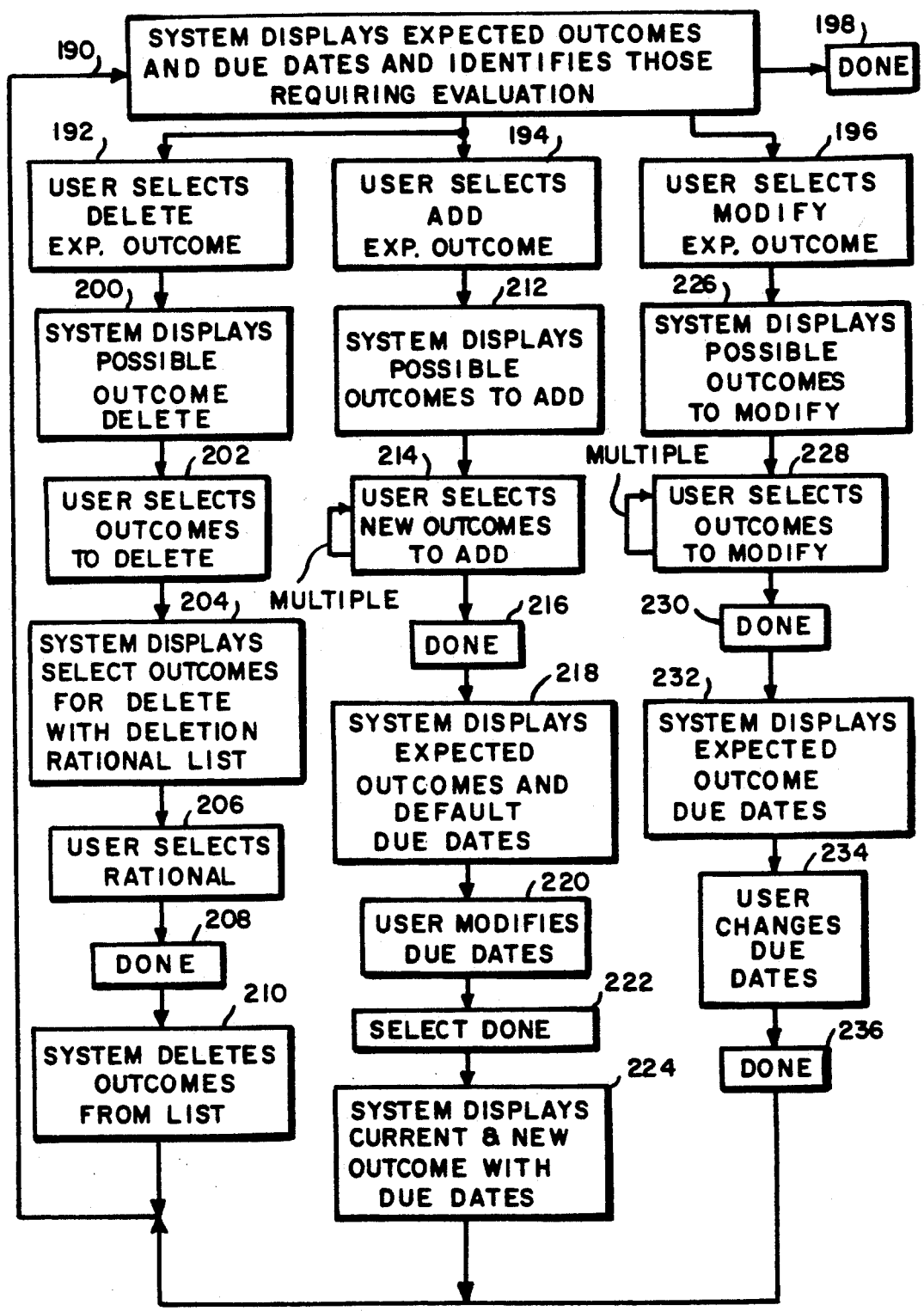
FIG. 3.6

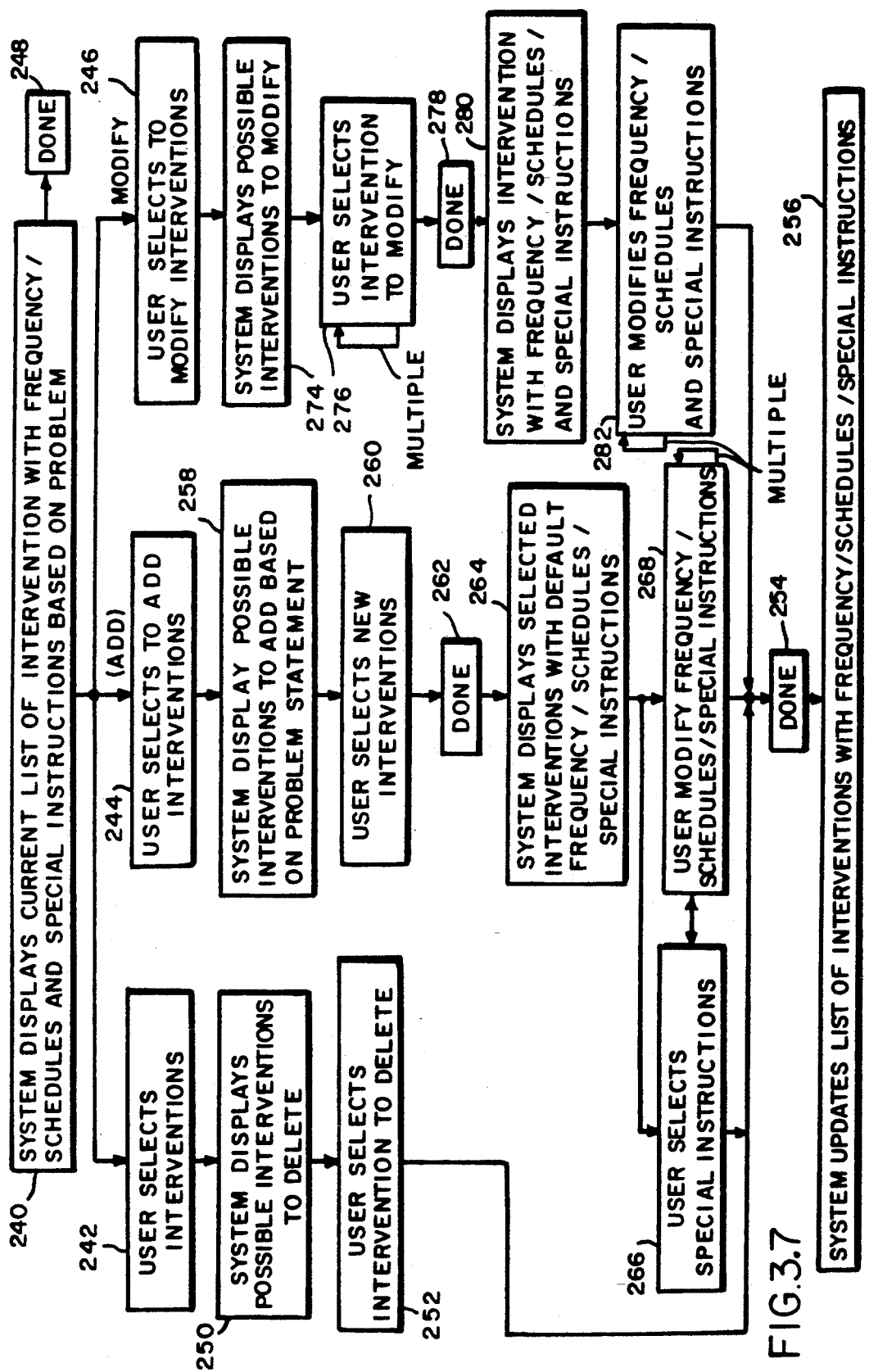
FIG.3.7

3 ICU WEST WATSON, LULU MRN #123-45678 DX: S/P CABG x 4

| MAIN MENU | DATA ENTRY | OPTIONS | PRINT | | HELP |

INDIVIDUAL PROBLEMS/DIAGNOSIS
SELECT FROM ALPHABETICAL LIST

- A - B
- C - D
- E - G
- H - K
- L - P
- Q - S
- T - Z
- CANCEL

STANDARD CARE PLANS
SELECT BODY SYSTEM TO INDEX CARE PLAN

- CARDIOVASCULAR
- NEUROLOGIC / NEUROSURGICAL
- RESPIRATORY
- GASTROINTESTINAL
- GENITOURINARY
- ENDOCRINE / METABOLIC
- INTEGUMENTARY / MUSCULOSKELETAL
- HEMATOLOGIC
- EENT
- PYSCHO / SOCIAL
- CANCEL

SYSTEM MESSAGE AREA          TUES 10 JAN 89  5:45 pm

FIG. 4

| NURSE CARE PLAN | 3 ICU WEST | WATSON, LULU MRN #123-45678 DX: S/P CABG x4 | | | HELP |

| MAIN MENU | DATA ENTRY | OPTIONS | PRINT | | |

STANDARD CARDIOVASCULAR CARE PLANS:

SELECT DIAGNOSIS:

- ANGINA PECTORIS
- ARRHYTHMIAS
- CARDIOGENIC SHOCK
- CORONARY ARTERY BYPASS GRAFT
- CONGESTIVE HEART FAILURE
- DIGITALIS TOXICITY
- HYPERTENSION
- MYOCARDIAL INFARCTION
- VENTRICULAR ANEURYSM
- VALVULAR HEART DISEASE

CANCEL

SYSTEM MESSAGE AREA — TUES 10 JAN 89 5:45 pm

FIG. 5

| NURSE CARE PLAN | 3 ICU WESTWATSON, LULU MRN #123-45678 DX: S/P CABG x4 | | | HELP |
|---|---|---|---|---|
| MAIN MENU | DATA ENTRY | OPTIONS | PRINT | |

CORONARY ARTERY BYPASS GRAFT DRG #106/107

CORONARY ARTERY BYPASS GRAFT : STD CARE PLAN

SELECT PROBLEM TO CHART ON:

- #1  KNOWLEDGE DEFICIT
- #2  INEFFECTIVE AIRWAY CLEARANCE
- #3  ALTERED CARDIAC OUTPUT: DECREASED
- #4  ARRYTHMIAS
- #5  ALTERATION IN TISSUE PERFUSION
- #6  POTENTIAL FOR FLUID VOLUME DEFICIT
- #7  POTENTIAL FOR INFECTION

[ACCEPT STD.C.P.]   [CANCEL]

PROBLEM #1: DATE DEFINED: 01/10/89
INEFFECTIVE AIRWAY CLEARANCE

SYSTEM MESSAGE AREA        TUES 10 JAN 89  5:45pm

FIG.6

| NURSE CARE PLAN | 3 ICU WESTWATSON, LULU MRN #123-45678 DX: S/P CABG x 4 | | HELP |
|---|---|---|---|
| MAIN MENU | DATA ENTRY | OPTIONS | PRINT |

CORONARY ARTERY BYPASS GRAFT DRG #106/107

PROBLEM #1: DATE DEFINED: 01/10/89
INEFFECTIVE AIRWAY CLEARANCE
ETIOLOGY: THICK VISCOUS BRONCHIAL SECRETIONS

□

---

CORONARY ARTERY BYPASS GRAFT: STD CARE PLAN
INEFFECTIVE AIRWAY CLEARANCE
SELECT ETIOLOGY:

- THICK VISCOUS BRONCHIAL SECRETIONS
- MUCOUS STASIS / PLUGGING
- NEUROMUSCULAR IMPAIRMENT
- DECREASED ENERGY OR FATIQUE
- PAIN
- OBSTRUCTION - TUMOR FOREIGN BODIES
- TRACHEOBRONCHIAL INFECTION
- TRAUMA
- PERCEPTUAL / COGNITIVE IMPAIRMENT
- SMOOTH MUSCLE CONSTRICTION (BRONCOSPASM)

| DONE | ACCEPT STANDARDS | ACCEPT ALL | CANCEL |

TUES 10 JAN 89 5:45pm

76

SYSTEM MESSAGE AREA

FIG. 7

| NURSE CARE PLAN | 3 ICU WESTWATSON, LULU MRN #123-45678 DX: S/P CABG x 4 | | | ? |
|---|---|---|---|---|
| MAIN MENU | DATA ENTRY | OPTIONS | PRINT | HELP |

CORONARY ARTERY BYPASS GRAFT DRG #106/107

PROBLEM #1: DATE DEFINED: 01/10/89
INEFFECTIVE AIRWAY CLEARANCE
ETIOLOGY: THICK VISCOUS BRONCHIAL SECRETIONS

□

←

---

CORONARY ARTERY BYPASS GRAFT: STD CARE PLAN

INEFFECTIVE AIRWAY CLEARANCE
SELECT EXPECTED OUTCOMES

- PT. CXRAY WILL BE CLEAR
- PT. WITHOUT SXS OR SYMPTOMS OF HYPOXIA
- BREATH SOUNDS CLEAR BILATERALLY
- PT. ABG's WNL
- PT. WILL BE ABLE TO COUGH/CLEAR AIRWAY

| DONE | ACCEPT STANDARDS | ACCEPT ALL | CANCEL |

→

SYSTEM MESSAGE AREA    TUES 10 JAN 89 5:45pm

FIG. 8

| NURSE CARE PLAN | 3 ICU WESTWATSON, LULU MRN #123-45678 DX: S/P CABG x 4 | | |
|---|---|---|---|
| MAIN MENU | DATA ENTRY | OPTIONS | PRINT |

? HELP

CORONARY ARTERY BYPASS GRAFT DRG #106/107   CORONARY ARTERY BYPASS GRAFT: STD CARE PLAN

PROBLEM #1: DATE DEFINED: 01/10/89
INEFFECTIVE AIRWAY CLEARANCE
ETIOLOGY: THICK VISCOUS BRONCHIAL SECRETIONS
EXPECTED OUTCOMES:
 #1 PT. CXRAY WILL BE CLEAR
    DUE DATE: 01/13/89
 #2 PT. WITHOUT SXS. OR SYMPTOMS OF HYPOXIA
    DUE DATE: 01/12/89
 #3 BREATH SOUNDS CLEAR BILATERALLY
    DUE DATE: 01/13/89

INEFFECTIVE AIRWAY CLEARANCE
EXPECTED OUTCOMES: DUE DATES

PT. CXRAY WILL BE CLEAR
DUE DATE: [ 01/13/89 ]

PT. WITHOUT SXS OR SYMPTOMS OF HYPOXIA
DUE DATE: [ 01/12/89 ]

BREATH SOUNDS CLEAR BILATERALLY
DUE DATE: [ 01/13/89 ]

DONE    ACCEPT ALL    CANCEL

SYSTEM MESSAGE AREA    TUES 10 JAN 89 5:45pm

FIG.9

| NURSE CARE PLAN | 3 ICU WESTWATSON, LULU MRN #123-45678 DX: S/P CABG x 4 |
|---|---|
| MAIN MENU | DATA ENTRY | OPTIONS | PRINT | | | HELP ? |

CORONARY ARTERY BYPASS GRAFT DRG #106/107

PROBLEM #1: DATE DEFINED: 01/10/89
INEFFECTIVE AIRWAY CLEARANCE
ETIOLOGY: THICK VISCOUS BRONCHIAL SECRETIONS
EXPECTED OUTCOMES:
*#1 PT. CXRAY WILL BE CLEAR
  DUE DATE: 01/13/89
*#2 PT. WITHOUT SXS. OR SYMPTOMS OF HYPOXIA
  DUE DATE: 01/12/89
*#3 BREATH SOUNDS CLEAR BILATERALLY
  DUE DATE: 01/13/89 ☐

CORONARY ARTERY BYPASS GRAFT: STD CARE PLAN
INEFFECTIVE AIRWAY CLEARANCE
SELECT INTERVENTIONS

- CPT
- POSTURAL DRAINAGE
- MAINTAIN ADEQ HYDRATION: xcc/kg
- AUSCULTATE LUNG FIELDS
- MONITOR: SIGNS OF RESP DISTRESS
- MONITOR: COLOR/AMT/CONSISTENCY SECRETIONS
- TCDB (TURN/COUGH/DEEP BREATHE)
- MONITOR: SOB / RETRACTIONS
- MONITOR: TOTAL BODY BALANCE
- SMOOTH MUSCLE CONSTRICTION (BRONCOSPASM)

| DONE | ACCEPT STANDARDS | ACCEPT ALL | CANCEL |

TUES 10 JAN 89  5:45pm

SYSTEM MESSAGE AREA

FIG. 10

| NURSE CARE PLAN | 3 ICU WESTWATSON, LULU MRN #123-45678 DX: S/P CABG x4 |
|---|---|
| MAIN MENU | DATA ENTRY | OPTIONS | PRINT | | | ? HELP |

CORONARY ARTERY BYPASS GRAFT DRG #106/107 | CORONARY ARTERY BYPASS GRAFT: STD CARE PLAN

PROBLEM #1: DATE DEFINED: 01/10/89
INEFFECTIVE AIRWAY CLEARANCE
ETIOLOGY: THICK VISCOUS BRONCHIAL SECRETIONS
EXPECTED OUTCOMES:
1 PT. CXRAY WILL BE CLEAR
   DUE DATE: 01/13/89
2 PT. WITHOUT SXS. OR SYMPTOMS OF HYPOXIA
   DUE DATE: 01/12/89
3 BREATH SOUNDS CLEAR BILATERALLY
   DUE DATE: 01/13/89 □

INEFFECTIVE AIRWAY CLEARANCE
SELECT INTERVENTIONS

- CPT
- POSTURAL DRAINAGE
- MAINTAIN ADEQ HYDRATION: xcc/kg
- AUSCULTATE LUNG FIELDS
- MONITOR: SIGNS OF RESP DISTRESS
- MONITOR: COLOR/AMT/CONSISTENCY SECRETIONS
- TCDB (TURN/COUGH/DEEP BREATHE)
- MONITOR: SOB / RETRACTIONS
- MONITOR: TOTAL BODY BALANCE
- SMOOTH MUSCLE CONSTRICTION (BRONCOSPASM)

| DONE | ACCEPT STANDARDS | ACCEPT ALL | CANCEL |

TUES 10 JAN 89 5:45pm

SYSTEM MESSAGE AREA

FIG.10A

| NURSE CARE PLAN | 3 ICU WEST | WATSON, LULU | MRN #123-45678 | DX: S/P CABG x 4 | |
|---|---|---|---|---|---|
| MAIN MENU | DATA ENTRY | OPTIONS | PRINT | | HELP |

CORONARY ARTERY BYPASS GRAFT  DRG #106/107

PROBLEM #1: DATE DEFINED: 01/10/89
INEFFECTIVE AIRWAY CLEARANCE
ETIOLOGY: THICK VISCOUS BRONCHIAL SECRETIONS
EXPECTED OUTCOMES:
1 PT. CXRAY WILL BE CLEAR
   DUE DATE: 01/13/89
2 PT. WITHOUT SXS. OR SYMPTOMS OF HYPOXIA
   DUE DATE: 01/12/89
3 BREATH SOUNDS CLEAR BILATERALLY
   DUE DATE: 01/13/89 ☐

CORONARY ARTERY BYPASS GRAFT: STD CARE PLAN
INEFFECTIVE AIRWAY CLEARANCE
INTERVENTIONS: FREQUENCY AND SCHEDULE

CPT:
FREQUENCY: q 4 hr
SCHEDULE: 6/10/2
SPECIAL INSTRUCTIONS

POSTURAL DRAINAGE:
FREQUENCY: q 4 hr
SCHEDULE: 6/10/2
SPECIAL INSTRUCTIONS

DONE        CANCEL

SYSTEM MESSAGE AREA          TUES 10 JAN 89  5:45pm

FIG. 11A

| NURSE CARE PLAN | 3 ICU WESTWATSON, LULU MRN #123-45678 DX: S/P CABG x 4 | | | ? HELP |
|---|---|---|---|---|
| MAIN MENU | DATA ENTRY | OPTIONS | PRINT | |

CORONARY ARTERY BYPASS GRAFT DRG #106/107 | CORONARY ARTERY BYPASS GRAFT: STD CARE PLAN

PROBLEM #1: DATE DEFINED: 01/10/89
INEFFECTIVE AIRWAY CLEARANCE
ETIOLOGY: THICK VISCOUS BRONCHIAL SECRETIONS
EXPECTED OUTCOMES:
 #1 PT. CXRAY WILL BE CLEAR
    DUE DATE: 01/13/89
 #2 PT. WITHOUT SXS. OR SYMPTOMS OF HYPOXIA
    DUE DATE: 01/12/89
 #3 BREATH SOUNDS CLEAR BILATERALLY
    DUE DATE: 01/13/89 ☐

INEFFECTIVE AIRWAY CLEARANCE
INTERVENTIONS: FREQUENCY AND SCHEDULE

CPT:
  FREQUENCY: q 4 hr
  SCHEDULE: 6/10/2

CPT: SPECIAL INSTRUCTIONS
  CONCENTRATE ON:
   R LOBES
   L LOBES
   RUL
   RML
   RLL
   LUL
   LLL
  DONE    CANCEL

POSTURAL DRAIN
FREQUENCY:
SCHEDULE:

DONE    CANCEL

TUES 10 JAN 89  5:45 pm

SYSTEM MESSAGE AREA

FIG. 11B

| NURSE CARE PLAN | 3 ICU WESTWATSON, LULU MRN #123-45678 DX: S/P CABG x4 | ? HELP |
|---|---|---|
| MAIN MENU | DATA ENTRY | OPTIONS | PRINT | | |

CORONARY ARTERY BYPASS GRAFT DRG #106/107

PROBLEM #1: DATE DEFINED: 01/10/89
INEFFECTIVE AIRWAY CLEARANCE
ETIOLOGY: THICK VISCOUS BRONCHIAL SECRETIONS
EXPECTED OUTCOMES:
1 PT. CXRAY WILL BE CLEAR
   DUE DATE: 01/13/89
2 PT. WITHOUT SXS. OR SYMPTOMS OF HYPOXIA
   DUE DATE: 01/12/89
3 BREATH SOUNDS CLEAR BILATERALLY
   DUE DATE: 01/13/89
INTERVENTIONS:
- CPT q4h SCHEDULE: 6/10/2/...
  SPECIAL INSTRUCTIONS: CONCENTRATE ON
  RML: LLL
- POSTURAL DRAINAGE q4h SCHEDULE: 5/9/1..
- MAINTAIN ADEQUATE HYDRATION: 2cc/kg
- AUSCULTATE LUNG FIELDS: q6h
  SCHEDULE: 8am/4pm/12am ▯

---

CORONARY ARTERY BYPASS GRAFT: STD CARE PLAN
INEFFECTIVE AIRWAY CLEARANCE
INTERVENTIONS: FREQUENCY AND SCHEDULE

MAINTAIN ADEQUATE HYDRATION

FREQUENCY: [CONTINUOUS]
AMOUNT: [2 cc/kg]
[SPECIAL INSTRUCTIONS]

AUSCULTATE LUNG FIELDS
FREQUENCY: [q 8 hr]
SCHEDULE: [8am/4pm/12am]
[SPECIAL INSTRUCTIONS]

[DONE]  [CANCEL]

TUES 10 JAN 89  5:45pm

SYSTEM MESSAGE AREA

FIG. 11C

| NURSE CARE PLAN | 3 ICU WESTWATSON, LULU MRN #123-45678 DX: S/P CABG x 4 | |
|---|---|---|
| MAIN MENU | DATA ENTRY | OPTIONS | PRINT | | ❓ HELP |

CORONARY ARTERY BYPASS GRAFT: STD CARE PLAN

INEFFECTIVE AIRWAY CLEARANCE
INTERVENTIONS: FREQUENCY AND SCHEDULE

TCDB (TURN / COUGH / DEEP BREATHE)

| q 4 hr | 2/6/10... | SPECIAL INSTRUCTIONS |

MONITOR SIGNS OF RESPIRATORY DISTRESS:
FREQUENCY: | CONTINUOUS |

SPECIAL INSTRUCTIONS
SIGNS OF RESPIRATORY DISTRESS:
DYSPNEA
NASAL FLARING
CYANOSIS
SOB
TACHYCARDIC

| CANCEL |

| DONE | | CANCEL |

---

CORONARY ARTERY BYPASS GRAFT DRG #106/107

PROBLEM #1: DATE DEFINED: 01/10/89
INEFFECTIVE AIRWAY CLEARANCE
ETIOLOGY: THICK VISCOUS BRONCHIAL SECRETIONS
EXPECTED OUTCOMES:
1 PT. CXRAY WILL BE CLEAR
   DUE DATE: 01/13/89
2 PT. WITHOUT SXS. OR SYMPTOMS OF HYPOXIA
   DUE DATE: 01/12/89
3 BREATH SOUNDS CLEAR BILATERALLY
   DUE DATE: 01/13/89
INTERVENTIONS:
- CPT q4h SCHEDULE: 6/10/2/...
  SPECIAL INSTRUCTIONS: CONCENTRATE ON
  RML: LLL
- POSTURAL DRAINAGE q4h SCHEDULE: 5/9/1/..
- MAINTAIN ADEQUATE HYDRATION: 2cc/kg
- AUSCULTATE LUNG FIELDS: q6h
  SCHEDULE: 8am/4pm/12am
- TCDB: q4h SCHEDULE: 12/4/8...
- MONITOR SIGNS OF RESPIRATORY DISTRESS:
  FREQUENCY: CONTINUOUS ▫

| SYSTEM MESSAGE AREA | | TUES 10 JAN 89  5:45pm |

FIG. 11D

| NURSE CARE PLAN | 3 ICU WESTWATSON, LULU MRN #123-45678 DX: S/P CABG x 4 |
|---|---|
| MAIN MENU | DATA ENTRY | OPTIONS | PRINT | | HELP ? |

CORONARY ARTERY BYPASS GRAFT DRG #106/107 | CORONARY ARTERY BYPASS GRAFT: STD CARE PLAN

PROBLEM #1: DATE DEFINED: 01/10/89
INEFFECTIVE AIRWAY CLEARANCE
ETIOLOGY: THICK VISCOUS BRONCHIAL SECRETIONS
EXPECTED OUTCOMES:
1 PT. CXRAY WILL BE CLEAR
   DUE DATE: 01/13/89
2 PT. WITHOUT SXS. OR SYMPTOMS OF HYPOXIA
   DUE DATE: 01/12/89
3 BREATH SOUNDS CLEAR BILATERALLY
   DUE DATE: 01/13/89
INTERVENTIONS:
- CPT q4h SCHEDULE: 6/10/2/...
  SPECIAL INSTRUCTIONS: CONCENTRATE ON
  RML: LLL
- POSTURAL DRAINAGE q4h SCHEDULE: 5/9/1...
- MAINTAIN ADEQUATE HYDRATION: 2cc/kg
- AUSCULTATE LUNG FIELDS: q6h
  SCHEDULE: 8am/4pm/12am
- TCDB: q4h SCHEDULE: 12/4/8...
- MONITOR SIGNS OF RESPIRATORY DISTRESS:
  FREQUENCY: CONTINUOUS ▢

SELECT PROBLEM TO CHART ON:

1 KNOWLEDGE DEFICIT
2 INEFFECTIVE AIRWAY CLEARANCE
3 ALTERED CARDIAC OUTPUT: DECREASED
4 ARRYTHMIAS
5 ALTERATION IN TISSUE PERFUSION
6 POTENTIAL FOR FLUID VOLUME DEFICIT
7 POTENTIAL FOR INFECTION

| ACCEPT STD.C.P. | CANCEL |

122

| SYSTEM MESSAGE AREA | TUES 10 JAN 89 5:45pm |

FIG. 12

| PROGRESS NOTES | 3 ICU WESTWATSON, LULU MRN #123-45678 DX: S/P CABG x 4 | | HELP |
|---|---|---|---|
| MAIN MENU | DATA ENTRY | OPTIONS | PRINT | | |

SELECT ACTIVE PROBLEM TO CHART ON:
DATE DEFINED PROB* PROBLEM

| DATE DEFINED | PROB* | PROBLEM | NURSE |
|---|---|---|---|
| 01/10/89 | 1 | INEFFECTIVE AIRWAY CLEARANCE R/T THICK BRONCHIAL SECRETIONS | BEP/RN |
| 01/10/89 | 2 | ALTERED CARDIAC OUTPUT: DECREASED R/T SURGERY | BEP/RN |
| 01/10/89 | 3 | ALTERATION IN TISSUE PERFUSION | BEP/RN |
| 01/10/89 | 4 | ARRYTHMIAS / COLLABORATIVE | BEP/RN |
| 01/10/89 | 5 | POTENTIAL FOR FLUID VOLUME DEFICIT | BEP/RN |
| 01/12/89 | 7 | POTENTIAL FOR INFECTION | MH/RN |
| 01/12/89 | 8 | KNOWLEDGE DEFICIT | MH/RN |
| | | | |
| | | | |
| | | | |

CANCEL

| SYSTEM MESSAGE AREA | | FRI 13 JAN 89 5:45pm |
|---|---|---|

FIG.14

| PROGRESS NOTES | 3 ICU WESTWATSON, LULU MRN #123-45678 DX: S/P CABG x 4 | | |
|---|---|---|---|
| MAIN MENU | DATA ENTRY | OPTIONS | PRINT | HELP |

PROBLEM *1: INEFFECTIVE AIRWAY CLEARANCE
ETIOLOGY: THICK VISCOUS BRONCHIAL SECRETIONS
S/O: ☐

INEFFECTIVE AIRWAY CLEARANCE
SELECT SUBJ./OBJ. DATE:

| | WNL | INCR. | DECR. | + |
|---|---|---|---|---|
| RR | | | | + |
| PT. REPORTS | SOB/DIFFICULTY BREATHING | | | + |
| PT. REPORTS | FEELING ANXIOUS | | | + |
| CYANOSIS | NONE | PRESENT | | + |
| DYSPNEA | NONE | ON EXERTION | | + |
| COUGH | EFFECTIVE | INEFFECTIVE | | + |
| COUGH | PRODUCTIVE | NON-PRODUCTIVE | | + |
| SPUTUM | NORMAL | ABNL | | + |
| WHEEZING | ABSENT | PRESENT | | + |
| RALES | ABSENT | PRESENT | | + |
| RHONCHI | ABSENT | PRESENT | | + |

DONE    CANCEL

SYSTEM MESSAGE AREA    FRI 13 JAN 89 5:45 pm

FIG. 15

| PROGRESS NOTES | 3 ICU WEST | WATSON, LULU | MRN #123-45678 DX: S/P CABG x 4 | |
|---|---|---|---|---|
| MAIN MENU | DATA ENTRY | OPTIONS | PRINT | |

PROBLEM #1: INEFFECTIVE AIRWAY CLEARANCE
ETIOLOGY: THICK VISCOUS BRONCHIAL SECRETIONS
S/O: RR INCREASED; CYANOSIS: NONE; DYSPNEA ON EXERTION. COUGH: EFFECTIVE; COUGH: PRODUCTIVE; SPUTUM: ABNL.. ▪

INEFFECTIVE AIRWAY CLEARANCE
SELECT SUBJ/OBJ. DATE:

| | WNL | INCR. | DECR. | |
|---|---|---|---|---|
| RR | | | | + |
| PT. REPORTS | SOB/DIFFICULTY BREATHING | | | + |
| PT. REPORTS | FEELING ANXIOUS | | | + |
| CYANOSIS | NONE | PRESENT | | + |
| DYSPNEA | NONE | ON EXERTION | | + |
| COUGH | EFFECTIVE | INEFFECTIVE | | + |
| COUGH | PRODUCTIVE | NON-PRODUCTIVE | | + |
| SPUTUM | NORMAL | ABNL | | + |
| WHEEZING | ABSENT | PRESENT | | + |
| RALES | ABSENT | PRESENT | | + |
| RHONCHI | ABSENT | PRESENT | | + |

DONE   CANCEL

FRI 13 JAN 89  5:45pm

HELP

SYSTEM MESSAGE AREA

PROGRESS NOTES | 3 ICU WEST | WATSON, LULU | MRN #123-45678 | DX: S/P CABG x 4

MAIN MENU | DATA ENTRY | OPTIONS | PRINT | | | HELP

PROBLEM #1: INEFFECTIVE AIRWAY CLEARANCE
ETIOLOGY: THICK VISCOUS BRONCHIAL SECRETIONS
S/O: RR INCREASED; CYANOSIS: NONE; DYSPNEA ON EXERTION. COUGH: EFFECTIVE; COUGH: PRODUCTIVE; SPUTUM: ABNL. SPUTUM CHARACTERISTICS: GREEN; THICK: C&S SENT. RALES: ABSENT. RHONCHI: ABSENT. ▪

INEFFECTIVE AIRWAY CLEARANCE
SELECT SUBJ/OBJ. DATE:

| | WNL | INCR. | DECR. |
|---|---|---|---|
| RR | | | |
| PT. REPORTS | SOB/DIFFICULTY BREATHING | | |
| PT. REPORTS | FEELING ANXIOUS | | |
| CYANOSIS | NONE | PRESENT | |
| DYSPNEA | NONE | ON EXERTION | |
| COUGH | EFFECTIVE | INEFFECTIVE | |
| COUGH | PRODUCTIVE | NON-PRODUCTIVE | |
| SPUTUM | NORMAL | ABNL | |
| WHEEZING | ABSENT | PRESENT | |
| RALES | ABSENT | PRESENT | |
| RHONCHI | ABSENT | PRESENT | |

DONE | CANCEL

SYSTEM MESSAGE AREA | FRI 13 JAN 89 5:45 pm

FIG. 18

| PROGRESS NOTES | 3 ICU WEST | WATSON, LULU | MRN #123-45678 | DX: S/P CABG x 4 | |
|---|---|---|---|---|---|
| MAIN MENU | DATA ENTRY | OPTIONS | PRINT | NEW E.O. | HELP ? |

PROBLEM #1: INEFFECTIVE AIRWAY CLEARANCE
ETIOLOGY: THICK VISCOUS BRONCHIAL SECRETIONS
S/O: RR INCREASED; CYANOSIS: NONE; DYSPNEA ON
EXERTION. COUGH: EFFECTIVE; COUGH:
PRODUCTIVE; SPUTUM: ABNL. SPUTUM
CHARACTERISTICS: GREEN; THICK; C & S SENT.
RALES: ABSENT. RHONCHI: ABSENT. ▫

INEFFECTIVE AIRWAY CLEARANCE
SELECT: PROGRESS TOWARDS OUTCOME:

E.O. 1 PT. CXRAY WILL BE CLEAR
DUE DATE: 01/13/89
OUTCOME STATUS:

| PT. PROGRESSING TOWARDS OUTCOME / NO CHANGES REQUIRED |
| PT. NOT ACHIEVING OUTCOME |
| PT. ACHIEVING OUTCOME, BUT PROGRESS SLOWER THAN EXPECTED. |
| PT. OUTCOME MET |

[DONE]  [CANCEL]

SYSTEM MESSAGE AREA                FRI 13 JAN 89  5:45 pm

FIG. 19

| PROGRESS NOTES | 3 ICU WEST | WATSON, LULU | MRN #123-45678 | DX: S/P CABG x 4 | ? HELP |

| MAIN MENU | DATA ENTRY | OPTIONS | PRINT | NEW E.O. | |

PROBLEM #1: INEFFECTIVE AIRWAY CLEARANCE
ETIOLOGY: THICK VISCOUS BRONCHIAL SECRETIONS
S/O: RR INCREASED: CYANOSIS: NONE: DYSPNEA ON
EXERTION. COUGH: EFFECTIVE: COUGH:
PRODUCTIVE; SPUTUM: ABNL. SPUTUM
CHARACTERISTICS: GREEN: THICK: C & S SENT.
RALES: ABSENT. RHONCHI: ABSENT.
O.S.: E.O.*1 PT. CXRAY WILL BE CLEAR
DUE DATE: 01/13/89
PROGRESS: PT. ACHIEVING OUTCOME, BUT
PROGRESS SLOWER THAN EXPECTED.
REASON(S): CXRAY INDICATES INFECTION.
INAPPROPRIATE INTERVENTIONS. ▪

---

INEFFECTIVE AIRWAY CLEARANCE
SELECT: PROGRESS TOWARDS OUTCOME:

E.O.*1 PT. CXRAY WILL BE CLEAR
DUE DATE: 01/13/89
OUTCOME STATUS:

PT. ACHIEVING OUTCOME, BUT
PROGRESS SLOWER THAN EXPECTED.
SELECT REASON(S):

| CXRAY INDICATES INFECTION |
| COMPLICATIONS POST-SURGERY |
| RESP STATUS COMPROMISED |
| MULTI-SYSTEM PROBLEMS |
| INAPPROPRIATE INTERVENTIONS |

[DONE]   [CANCEL]

[DONE]   [CANCEL]

---

SYSTEM MESSAGE AREA         FRI 13 JAN 89 5:45 pm

FIG. 20

| PROGRESS NOTES | 3 ICU WEST WATSON, LULU MRN #123-45678 DX: S/P CABG x 4 | | HELP |
|---|---|---|---|
| MAIN MENU | DATA ENTRY | OPTIONS | PRINT | NEW E.O | | |

PROBLEM #1: INEFFECTIVE AIRWAY CLEARANCE
ETIOLOGY: THICK VISCOUS BRONCHIAL SECRETIONS
S/O: RR INCREASED: CYANOSIS: NONE: DYSPNEA ON
EXERTION. COUGH: EFFECTIVE: COUGH:
PRODUCTIVE; SPUTUM: ABNL. SPUTUM
CHARACTERISTICS: GREEN: THICK: C & S SENT.
RALES: ABSENT. RHONCHI: ABSENT. ☐
O.S.: E.O.#1 PT. CXRAY WILL BE CLEAR
DUE DATE: 01/13/89
PROGRESS: PT. ACHIEVING OUTCOME, BUT
PROGRESS SLOWER THAN EXPECTED.
REASON(S): CXRAY INDICATES INFECTION.
INAPPROPRIATE INTERVENTIONS.

INEFFECTIVE AIRWAY CLEARANCE
SELECT: PROGRESS TOWARDS OUTCOME:

E.O.#1 PT. CXRAY WILL BE CLEAR
DUE DATE: 01/13/89
OUTCOME STATUS:

OUTCOME DUE DATE:
01/13/89

ATTENTION!
OUTCOME DUE TODAY!
OUTCOME DUE DATE
MUST BE CHANGED

ACCEPT

DONE    CANCEL

SYSTEM MESSAGE AREA            FRI 13 JAN 89 5:45 pm

FIG. 21

| PROGRESS NOTES | 3 ICU WESTWATSON, LULU MRN #123-45678 DX: S/P CABG x 4 | HELP |

| MAIN MENU | DATA ENTRY | OPTIONS | PRINT | NEW E.O. |

PROBLEM #1: INEFFECTIVE AIRWAY CLEARANCE
ETIOLOGY: THICK VISCOUS BRONCHIAL SECRETIONS
S/O: RR INCREASED: CYANOSIS: NONE: DYSPNEA ON
EXERTION. COUGH: EFFECTIVE: COUGH:
PRODUCTIVE; SPUTUM: ABNL. SPUTUM
CHARACTERISTICS: GREEN: THICK: C & S SENT.
RALES: ABSENT. RHONCHI: ABSENT.
O.S.: E.O.*1 PT. CXRAY WILL BE CLEAR
DUE DATE: 01/13/89
PROGRESS: PT. ACHIEVING OUTCOME, BUT
PROGRESS SLOWER THAN EXPECTED.
REASON(S): CXRAY INDICATES INFECTION.
INTERVENTIONS INAPPROPRIATE.
NEW DUE DATE: 01/15/89 ☐

INEFFECTIVE AIRWAY CLEARANCE
SELECT: PROGRESS TOWARDS OUTCOME:

E.O.*1 PT. CXRAY WILL BE CLEAR
DUE DATE: 01/13/89
OUTCOME STATUS:

PT. ACHIEVING OUTCOME, BUT
PROGRESS SLOWER THAN EXPECTED.
SELECT REASON(S)

DUE DATE:
01/15/89

[ACCEPT]

[DONE]   [CANCEL]

| SYSTEM MESSAGE AREA | FRI 13 JAN 89 5:45 pm |

FIG. 22

| PROGRESS NOTES | 3 ICU WEST | WATSON, LULU | MRN #123-45678 | DX: S/P CABG x 4 | |
|---|---|---|---|---|---|
| MAIN MENU | DATA ENTRY | OPTIONS | PRINT | NEW E.O. | HELP |

PROBLEM #1: INEFFECTIVE AIRWAY CLEARANCE
ETIOLOGY: THICK VISCOUS BRONCHIAL SECRETIONS
S/O: RR INCREASED; CYANOSIS: NONE; DYSPNEA ON
EXERTION. COUGH: EFFECTIVE; COUGH:
PRODUCTIVE; SPUTUM: ABNL. SPUTUM
CHARACTERISTICS: GREEN; THICK; C & S SENT.
RALES: ABSENT. RHONCHI: ABSENT.
O.S.: E.O. *1 PT. CXRAY WILL BE CLEAR
DUE DATE: 01/13/89
PROGRESS: PT. ACHIEVING OUTCOME, BUT
PROGRESS SLOWER THAN EXPECTED.
REASON(S): CXRAY INDICATES INFECTION.
INTERVENTIONS INAPPROPRIATE.
NEW DUE DATE: 01/15/89
E.O. *2 PT. WITHOUT SXS OR
SYMPTOMS OR HYPOXIA
DUE DATE: 01/13/89
PROGRESS: PT. OUTCOME MET. ☐

INEFFECTIVE AIRWAY CLEARANCE
SELECT: PROGRESS TOWARDS OUTCOME:

E.O.*2 PT. WITHOUT SXS OR
SYMPTOMS OR HYPOXIA
DUE DATE: 01/13/89
OUTCOME STATUS:

| PT. PROGRESSING TOWARDS OUTCOME /
NO CHANGES REQUIRED |

| PT. NOT ACHIEVING OUTCOME |

| PT. ACHIEVING OUTCOME. BUT
PROGRESS SLOWER THAN EXPECTED. |

| PT. OUTCOME MET |

| DONE | CANCEL |

SYSTEM MESSAGE AREA           FRI 13 JAN 89  5:45 pm

| PROGRESS NOTES | 3 ICU WESTWATSON, LULU MRN #123-45678 DX: S/P CABG x 4 | | | |
|---|---|---|---|---|
| MAIN MENU | DATA ENTRY | OPTIONS | PRINT | HELP |

PROBLEM #1: INEFFECTIVE AIRWAY CLEARANCE
ETIOLOGY: THICK VISCOUS BRONCHIAL SECRETIONS
S/O: RR INCREASED:CYANOSIS:NONE:DYSPNEA ON
EXERTION.COUGH:EFFECTIVE:COUGH:
PRODUCTIVE;SPUTUM: ABNL.SPUTUM
CHARACTERISTICS: GREEN:THICK:C & S SENT.
RALES: ABSENT. RHONCHI: ABSENT.
O.S.: E.O. #1 PT. CXRAY WILL BE CLEAR
DUE DATE : 01/13/89
PROGRESS: PT. ACHIEVING OUTCOME, BUT
PROGRESS SLOWER THAN EXPECTED.
REASON(S): CXRAY INDICATES INFECTION.
INTERVENTIONS INAPPROPRIATE.
NEW DUE DATE : 01/15/89
E.O. #2 PT. WITHOUT SXS OR
SYMPTOMS OR HYPOXIA
DUE DATE : 01/13/89
PROGRESS: PT. OUTCOME MET
PLAN:

INEFFECTIVE AIRWAY CLEARANCE
CURRENT INTERVENTIONS ACTIVATED
SELECT NEW OR MODIFY ACTIVE INTERVENTIONS:

- CPT q4h 6/10/2... CONO. ON RML:LLL
- POSTURAL DRAINAGE q4h 5/9/1...
- MAINTAIN ADEQUATE HYDRATION : 2cc/kg
- AUSCULATATE LUNG FIELDS: q6h 8am/4pm/12am
- MONITOR SIGNS OF RESP DISTRESS: CONTINUOUS
- TCDB q4h 2/6/10
- MONITOR: COLOR/AMT/CONSISTENCY SECRETIONS
- MONITOR: SOB / RETRACTIONS
- MONITOR: TOTAL BODY BALANCE
- SMOOTH MUSCLE CONSTRICTION

[DONE] [CANCEL]

SYSTEM MESSAGE AREA          FRI 13 JAN 89  5:45 pm

FIG. 26

METHOD AND APPARATUS FOR PERFORMING PATIENT DOCUMENTATION

FIELD OF THE INVENTION

This invention relates to methods and apparatus for performing patient documentation at a health care facility, and more particularly to a system which permits an initial health care plan to be generated for a patient by a health care professional using for the most part coded standardized inputs, and for the plan to be automatically updated as progress notes are generated on the patient's care, with the complete patient care plan history being retained in the system for archival purposes.

BACKGROUND OF THE INVENTION

While many aspects of operation and administration at hospitals and other health care facilities have been computerized over the past years, one of the most important aspects, the generating of patient care or health plans, the updating of these plans and the generation of progress notes by health care professionals, such as doctors, nurses, therapists, and the like, is still performed largely by hand. As a result, while a care plan of some type is normally generated shortly after a patient is admitted to a particular service, for example an intensive care unit (ICU), cardiac surgery unit, or the like, this care plan is seldom referred to thereafter and is seldom if ever updated to reflect actual progress by the patient.

Another problem is that, since the care plan is not referred to in most cases when the professional is preparing progress notes on the patient, there is no check to assure that the original care plan has in fact been followed, or that proposed resolution dates in the original care plan have been met or updated. When changes in the original care plan are made as a result of changes in patient status, such changes are frequently not entered with the original care plan, and no good archival record is generally maintained of car plan changes. The professional notes for a particular patient frequently do not have available an updated version of the patient's care plan. Further, even though a form may be available for progress notes, the form does not take into account the unique problems of the individual patient, and does not give the professional a checklist of items to be investigated for such problems or suggested interventions or resolution dates for the particular patient problem. When changes are made or expected outcomes are not achieved, the reasons for such occurrences are seldom provided, making any further review far more difficult. Again, a good archival record of what has been done for the particular patient is not readily available.

Because of the absence of good archival records, and the absence of reasons for changes or deviations, tracking a problem for quality control, legal or other reasons is difficult, and it is difficult to research the relative effectiveness of various interventions or to perform other research from the records.

Even with computer based patient health plans and/or progress note systems, many of the problems indicated above still exist. Such systems also, in many instances, lack flexibility so as to be configurable by the user as to indexes and problems; problems, outcomes, interventions and the like for a given problem; default frequencies and schedules for interventions and due dates for outcomes, etc. In addition, they frequently do not give the user the ability to add special instructions or to add items as required. Further, it is generally not possible to obtain either an updated care plan or a historical care plan on request.

A need therefore exists for an improved hospital patient documentation method and apparatus which facilitates the generation of the initial care/health plan by providing the health care professional or other user with preselected options at each stage in the procedure which a user can quickly and easily select by use of a cursor or other suitable means. The user should preferably be able to see the plan as it develops in addition to viewing the available options at each stage in the development. It is also preferable that each menu item placed in the system be coded to facilitate performing computer searches on such items, thereby facilitating the use of the system for audit, quality control, legal, research, or other purposes.

It is further desirable that progress notes also be produced from a menu driven system, with the menu items being keyed to the particular problems for the particular patient, and any changes made in the care/health plan as a result of changes in patient status as documents in the progress notes be utilized to automatically update the care/health plan. However all versions of the care plan, including the initial care plan, and all updates should be stored in the system, preferably in coded form, to again facilitate various search activities.

SUMMARY OF THE INVENTION

In accordance with the above, this invention provides a hospital patient documentation method and apparatus (the method and apparatus sometimes hereinafter being collectively referred to as "system") which is used to generate an initial care/health plan for the patient, the plan identifying the patient's health problems, the problem cause(s), the expected outcomes, and the health interventions to achieve such outcomes. Various support data, such as signs and symptoms, may also be entered. The system also provides for the periodic entering of progress notes on the patient, with the system automatically updating the care plan for the patient in response to the progress notes. The system stores both the initial care plan and all of the updates thereof so that an audit trail of the patient care and progress is maintained. The system includes a display, the care plan being generated by displaying an initial menu, and then displaying subsequent menus in response to each selection from a prior menu, until the care plan is completed. The menu items, while displayed in visually readable form, are coded in the system so the system may easily perform searches on a particular code for all entries involving such codes. The system also provides for the addition of entries to at least selected ones of the menus and for alterations in at least selected ones of the menus in response to inputs from the system user who would typically be a health care professional.

In generating a care plan, an initial menu might include an indication of body or other indexing system categories with potential diagnoses or other problem categories for each indexing system being displayed in a subsequent menu and potential problems associated with the problem category in still a further menu. The menus might then continue with menu selected etiologies and expected outcomes being displayed in response to the selection of a particular problem and outcome due dates automatically generated by the system being displayed in response to the user selecting one or more outcomes. The user may either accept or change the outcome due dates indicated by the system. The system may also display a menu of potential interventions for a selected outcome, and may automatically display frequency and schedule for each selected intervention. The system may also permit the user to indicate special instructions for each intervention. Menus may also be provided to permit entry of signs, symptoms and other support data. A running record of all selections made from the menus during the preceding steps is maintained, this running record constituting the health care plan. The display preferably has a split screen with menus being displayed on one part of the screen and the running record constituting the care plan to that point appearing on the other portion of the screen.

When the system user indicates a desire to enter a progress note, a menu of progress note options is preferably displayed. In response to the selecting of a progress note option, such as charting on an active problem, or adding a new problem which a patient is experiencing, appropriate problems for the particular patient are displayed. The use then selects the problem to be charted on or new problem and the system displays a menu for use by the user, which menu is appropriate for the selected problem. Again, it is preferable that a split screen is employed with the menu being displayed on one side of the screen and the user selections from the menu on the other side. The user may make modifications in any item entered earlier, and may evaluate patient progress toward expected outcomes. The evaluation may include reasons for deviations, and reasons may also be selected from menus or otherwise provided for other changes made in generating a progress note. Updated progress notes are recorded for both progress notes and as an updated care plan.

The foregoing and other objects, features and advantages of the invention will be apparent from the following more particular description of a preferred embodiment of the invention as illustrated in the accompanying drawings.

IN THE DRAWINGS

FIG. 1 is a block diagram of a data processing system suitable for use in practicing the teachings of this invention.

FIG. 2.0 is an overview flow diagram of the process for generating a patient care or health plan for a preferred embodiment.

FIGS. 2.1–2.7 are flow diagrams of the steps 2.1–2.7, respectively, of FIG. 2.0. Step 2.6A is included in FIG. 2.6.

FIG. 3.0 is an overview flow diagram of the progress notes operation for a preferrred embodiment of the invention.

FIGS. 3.1–3.7 are flow diagrams of the steps 3.1–3.7, respectively, shown in FIG. 3.0.

FIGS. 4–10, 10A, 11A–11D, and 12 show illustrative screen displays which might be generated during the generation of a patient health plan utilizing the process shown in FIG. 2.0.

FIGS. 13–26 show illustrative screen displays which might be generated during a progress notes operation performed in accordance with the process of FIG. 3.0.

DETAILED DESCRIPTION

Figure 1:
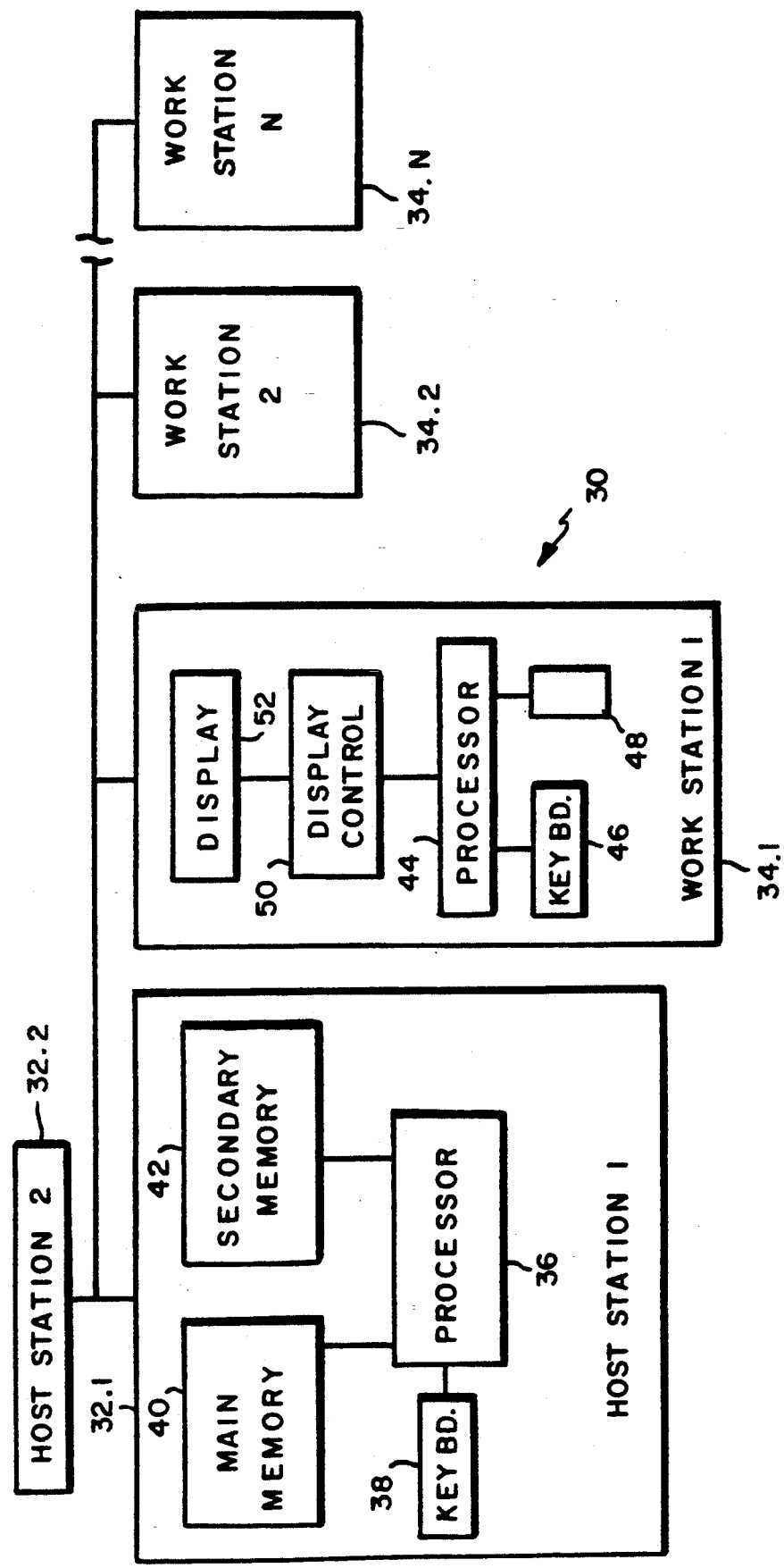

Referring first to FIG. 1, the system 30 has two host stations 32.1 and 32.2 and a plurality of work stations 34.1–34.N. Each host station has a processor 36 with one or more input devices such as a keyboard 38. Processor 36 also has a main memory 40 and a secondary memory 42. Components 36, 38, 40 and 42 may be standard components for performing the indicated functions. Processer 36 may, for example, be a HP375, with memory 40 being a 24 megabyte RAM and memory 42 a 660 megabyte hard disk system.

Each work station 34 also has a processor 44 which would typically be a smaller processor than the processor 36. Processor 44 includes a certain amount of internal memory, for example 12 megabytes, and would typically also have a disk drive or other secondary memory. Processor 44 also has various input devices such as keyboard 46 and a track ball 48. Each processor 44 operates a standard display controller 50 which, in turn, controls a display device 52 at the work station. Display device 52 would typically be a cathode ray tube screen, but could be some other type of standard display monitor.

In use, host stations 32 would be located at the same or separate central locations in the hospital or other health care facility, with each work station 34 being located at a nursing station, patient's room or other location where health care services are being provided. Each host station 32 has stored in its memory complete information on patients at the facility and updates to such information from a particular work station 34 are made to the memories of both host stations. However, care and support services for a particular work station are normally provided from one or the other of the host stations. Thus, major executables for the system such as reports, information gathering from monitors and the like are performed at the host station 32 associated with a given work station for that work station. However, application programs such as those for patient health plan and progress note generation are run at a work station 34. This permits a faster and more efficient system. However, since all patient information is stored at both host stations, in the event of a failure of one host station, the system can still operate in a manner which is substantially transparent to the users, except possibly for an increase in response time from the host. The likelihood of data being lost or being unable to properly maintain records on a patient is therefore minimized.

FIG. 2.0 is a general flow diagram for the process of generating a patient health plan (PHP) or care plan in accordance with this invention. The first step in this operation, step 2.1, involves entering the initial patient health plan application. This involves getting into the system through a suitable indexing system to reach the problem being experienced by the given patient. The selections from menus in the indexing system will, as will be discussed in greater detail later, result in a menu of selected problem categories being listed from which the user may select a problem category which is appropriate for the particular user This results in the display of a menu of problems in the particular category from which a user may again select a problem appropriate to the patient. Once the user selects a problem to be charted on, the operation proceeds to step 2.3 during which a menu of etiologies or causes for the particular problem are displayed. The user then selects the appropriate one or more etiologies from the menu.

During step 2.4, the next step in the operation, the user is presented with a menu of signs and symptoms or other supporting data relating to the selected problem and makes appropriate selections from the supporting data. The operation then proceeds to step 2.5 during which expected outcomes from the particular problem, including projected dates when such outcomes should occur, are listed. The user may accept the listed outcomes and dates, select only certain of the listed outcomes and dates, select outcomes with changed dates, or add new outcomes with projected completion dates.

When this operation has been completed, the user may be presented, during step 2.6, with a listing of possible interventions which might facilitate the desired outcomes. The interventions may also include standard frequencies, schedules, dosages, and special instructions. All of the above may be changed or supplemented by the user as appropriate.

Once step 2.6 has been completed, the user may return to step 2.2 to select a new problem from the previously selected problem category or to select a new problem category and an additional problem. Steps 2.3 through 2.6 would then be performed for the new problem and this process would be repeated until all problems appropriate to the patient have been entered into the system. At this point, the patient health plan is complete and the user indicates this by operating a "DONE" control during step 2.6A. The user may then elect to store the patient health plan which has just been generated in the program note section of the memory for the patient. All of the information generated during steps 2.2–2.6 for each problem are also stored as a patient health plan for the patient, except for the support data generated during step 2.4 which is only stored in the program notes. While this is true for the preferred embodiment of the invention, it is by no means a limitation on the invention and it is possible that, in a given system, the support data would also be stored as part of the patient health plan.

The steps just described would normally be performed soon after the patient enters the hospital, and preferably within 24 hours of such entrance. The particular menus, the due dates based on estimated time for an expected outcome to occur and the frequency, schedule, dosage, and special instructions for a given problem may be included with a system based on data accumulated from health care facilities of the type in which the system is being utilized, or may be wholly or partially customized by the given health care facility. Thus, the system may be custom configured based on the needs and experience at a given facility and health care professionals at a given facility are afforded the opportunity to use common criteria in generating a patient's health plan and to use standardized time schedules and the like in such a plan, but are also given freedom to make such variations in the standards as ma be appropriate for a given patient or condition.

One large advantage of utilizing a menu driven system such as that described above is that it permits the system to have a code for each menu entry which is stored in the system when an entry is made. The system may either automatically generate a code or require the user to provide a code for any new entries which the user makes. Thus, it is easy for the system to search the system based on any problem or other care plan item for various record keeping, archival, research or evaluation purposes. Such a capability does not exist in most current systems.

FIG. 2.1 further illustrates the initial step 2.1 in the generation of a patient health plan and FIG. 4 is a screen display useful in performing this step. Referring to FIG. 2.1 and to FIG. 4 together, the first step in the operation involves obtaining a screen display which provides one or more menus of indexing systems. This screen display is obtained by indicating to the system in a suitable coded manner, probably from a master system menu, that a patient health plan is to be generated. The information at the top of the screen concerning the patient's name, location, social security number and the like may be initially entered by the user or may be obtained from the system in response to an initial input from the user indicating the patient's name, number, or other identifying information. The date and time in the lower right-hand portion of the screen are automatically generated by the system. While this time has been shown as constant on the various screen displays utilized for the generation of a patient health plan, in practice this time would normally increase on a real time basis as the health plan is being generated.

FIG. 4 shows two indexing systems which may be utilized, probably alternatively, to initially get into the system to obtain a desired problem category. On the right-hand side of the screen, a plurality of body systems are listed which should include most body systems on which medical care may be required. If, as in the illustrative example, the patient has undergone a coronary artery bypass graft, problems relating to this procedure might be obtained by selecting the cardiovascular body system as shown in FIG. 4. The selection of the cardiovascular system may be accomplished using any standard technique for making selections from a menu, such as entering a shaded letter on the work station keyboard 46. For the preferred embodiment, the selection is made by operating a track ball 48 to move a cursor to the desired menu item. Selection is then made by operating a suitable key on keyboard 46, such as an "enter" key, a button on track ball device 48 or by other suitable means.

However, it is possible that the patient's problem may not be limited to a single body system. The left-hand side of FIG. 4 shows an alternative way of indexing into problem categories based on an alphabetic menu list. Thus, if the patient's problem resulted from a trauma such as a fall or auto accident, the user might make an appropriate menu selection such as "E-G" for a fall victim.

While two indexing categories are shown in FIG. 4, namely, body systems and alphabetical, it is to be understood that these are merely exemplary of available indexing systems and that a given health care facility, or service in such facility, might configure a different indexing system. It is also possible that for a medical facility, or a service within such facility, which provides specialized services, step 2.1 may be eliminated entirely and the initial display may be of problem categories.

From step 2.1, the operation proceeds to step 2.2 which is a flow diagrammed in FIG. 2.2. FIGS. 5 and 6 are displays which may be utilized in conjunction with this step. Referring to FIG. 2.2, the first step in this operation, step 60, is for the system to display problem categories. Assuming that during step 2.1, "Cardiovascular" was selected as the indexing system, a display of problem categories for cardiovascular might be as shown in FIG. 5. In FIG. 5, the problem categories are based on a diagnosis of the patient's problem. However, diagnosis may not always be the best way to organize problem categories. Thus, for example, if the body system were "integumentary/musculoskeletal", the problem categories might be indexed by body location, for example, the head, back, chest, right arm, etc.

During step 62, the user makes a selection from the problem categories displayed during step 60. In FIG. 5, this is accomplished by, for example, operating track ball 48 to highlight "Coronary Artery Bypass Graft" and then entering this menu selection in the a suitable manner as previously described.

During step 64, the next step in the operation, the user is provided with a display of problems in the selected problem category. FIG. 6 is an illustration of a potential display of problems for the problem category previously selected from the display in FIG. 5. The display shown in FIG. 6 has two halves; a right half which contains the menu of problems and a left half which contains a record of what has been selected so far. In this case, the left half contains an indication of the problem which is currently being highlighted on the right side menu.

At the bottom of the menu on the right side of the display are two areas which are indicated as "Accept Standard Care Plan" and "Cancel". Moving the cursor to Cancel and operating the appropriate enter key, button or other input element will cause the display to return to the previous menu level. For each menu level, there may be one or more menu items which are highlighted which are the standard items in a care plan for the given problem at that menu level. The user may accept such one or more menu items for the care plan by moving the cursor to the Accept Std. C.T. area on the display and doing an enter function. The user always has the option of selecting his own menu items rather than the standard before doing an enter.

Finally, if the problem which the user wishes to chart on does not appear in the menu shown in FIG. 6, the user may be provided with the option of adding an additional one or more menu items. The user may, for example, enter this mode through a selection from the "Data Entry" area at the top of the screen display. This might cause a menu to appear, one item of which could be "Enter New Problem". The user could then select this option and follow instructions provided for entering a new problem.

During step 66, the user selects the problem to be charted on from the menu (such as that shown in FIG. 6) by a suitable cursor movement. When this is done, the system assigns a number to the problem during step 68. For example, the "Ineffective Airway Clearance" problem selected from the display in FIG. 6 is indicated as problem No. 1. Finally, during step 70, the system displays the selected problem along with the problem number on the left-hand side of the screen.

At this point it should be noted that each men entry in the system has a coded value or number associated with it. Any entries made by the user also have a coded value assigned to them. The host processors keep track of these coded values so that the coded values may be utilized later for record-keeping, archival, diagnostic, research or other purposes.

From step 2.2, the operation proceeds to step 2.3 where the user selects the appropriate etiology. This step is shown in FIG. 2.3 and an illustrative display for this step is shown in FIG. 7. The first step in this operation, step 72, involves the system displaying possible etiologies or causes for the problem which was selected during step 2.2. Thus, if the problem is "Ineffective Airway Clearance", this may result from a variety of causes such as "thick viscous bronchial secretions", a "plugging", "a neuromuscular impairment", etc. There may be multiple causes for the problem. Therefore, during step 74, the user may make multiple selections from the menu. At the bottom of the menu, the user is provided with the option of accepting the standard, which in this case is the initially highlighted first item, or of accepting all of the listed etiologies. As with previous menus, the user may also select any combination of the menu items and ma add additional etiologies if desired.

When the user has selected all of the etiologies which the user wishes to select, the user may move the cursor to the "Done" area 76 on the screen and enter this selection in a suitable way (step 78). The operation then proceeds to step 80 to display the selected etiologies with the problem statement on the left-hand side of the screen. This is also shown in FIG. 7.

The problem, problem number and etiologies are hereinafter sometimes referred to as the "Problem Statement".

Once step 2.3 has been completed, the operation proceeds to step 2.4 to select support data for the given problem and etiology. FIG. 2.4 is a more detailed flow diagram of the operations performed during step 2.4. This is an optional step which is not illustrated by the screen displays. Typically, this would involve the system displaying possible supporting data which would be signs and symptoms associated with the particular condition. Such signs and symptoms might be things such as "wheezing", "patient short of breath", "poor patient color", "low-grade fever", "high fever", etc. During step 84, the user would select appropriate ones of such signs and symptoms. Again, this could be done using an Accept Standard screen area, and Accept All screen area, or by other suitable means previously discussed. When the selection of supporting data is complete, the user selects the "Done" area on the screen, step 86, and the system proceeds to display the appropriate supporting data with the problem statement (step 88). If supporting data is entered into the system during step 2.4, as will be discussed later, this information is stored as part of the progress notes, but is not included in the patient health plan.

The next step in the operation is step 2.5 during which the user selects expected outcomes. A flow diagram of step 2.5 for a preferred embodiment of the invention is shown in FIG. 2.5 and screen displays suitable for use in performing this step are illustrated in FIGS. 8 and 9. The first step in this operation is step 90 during which a display of possible expected outcomes is provided for the selected problem. FIG. 8 shows a menu of potential selected outcomes for the problem previously selected.

During step 92, the user selects the one or more expected outcomes which are appropriate. For purposes of illustration, the standard highlights the first three expected outcomes so that these outcomes may be selected by merely placing the cursor on the "Accept Standard" area and entering. Similarly, all the expected outcomes can be selected by entering the "Accept All" indication. Any other combination of the expected outcomes may also be selected. When the desired expected outcomes have been selected, the "Done" area of the display is entered (step 94), causing the operation to proceed to step 96. During this step, as illustrated by FIG. 9, the systems displays the expected outcomes selected during the previous operation on the left side of the display and displays an indication of due dates for the expected outcome on the right side. The due dates are based on the current date and the time, previously determined, which would normally be required for the expected outcome to occur. The user may change any of the expected outcome dates for the particular patient based on the user's assessment of the patient's condition and, as a result thereof, as to whether the expected outcome is likely to be achieved within the standard time. Such modifications are performed during step 98. If no modifications are required, the user may go to the "Accept All" area of the display.

When acceptable dates are being displayed, the user may select the "Done" area of the display (step 100), causing the operation to proceed to step 102 during which the system displays the outcomes with the due dates and problem statement. This is shown on the left side of FIG. 9.

When step 2.5 has been completed, the operation proceeds to step 2.6 during which the user defines interventions appropriate for achieving the desired outcomes for the selected problem. In some instances, the interventions may be the same for a given problem regardless of the selected outcomes, while in others the interventions may be outcome dependent. The interventions are always linked to, or in other words a function of, the problem. FIG. 2.6 is a more detailed flow diagram of the select interventions step. FIGS. 10 and 10A and 11A-11D are screen displays which might be utilized in performing this step.

The first step in this operation, step 104, is to display possible interventions for the select problem. FIG. 10 illustrates a possible screen display for this step in the operation for the problem selected in the previous screen displays. In this situation, the first four interventions are highlighted as the standard. During step 106, the next step in the operation, the user may either select the standard in the manner previously indicated, accept all of the interventions, or select any combination of the interventions. As before, additional interventions may also be added.

When all desired interventions have been selected, the operation proceeds to step 108 during which the "Done" area on the screen is selected. FIG. 10A shows the display of FIG. 10 wherein two interventions in addition to the standard interventions have been selected and the "Done" area has also been selected. This causes the operation to proceed to step 110 during which the system displays the selected interventions with default frequency, schedules and possibly special instructions. An examplary such display for the first two interventions is shown in FIG. 11A. From step 110, the operation proceeds to steps 112 and 114 wherein the user may enter or change special instructions or may modify frequencies and schedules for each intervention. For example, referring to FIG. 11B, special instructions for the CPT intervention are displayed. The user has selected two of the special instructions as being appropriate and these instructions are entered. In FIG. 11C, it is seen that the interventions with the frequency and schedule and the selected special instructions appear in the left-hand screen. In FIG. 2.6, this is accomplished by selecting "Done" during step 116 which causes the indicated display to appear during step 118.

From step 118, there are two options. In this instance, since only two interventions were initially displayed while six interventions were originally selected, there are additional interventions. Therefore, the operation proceeds through step 120 to return to step 110 for the additional interventions which are shown displayed in FIG. 11C. The operation then proceeds through steps 110, 112, 114, 116 and 118 for the additional interventions which it is assumed are not changed, and through step 120 to cause the final set of interventions to be displayed as seen in FIG. 11D. In this figure, special instructions previously provided are being canceled and the schedule for the TCDB intervention is being changed from 12/4/8 to 2/6/10. The numbers indicated are the hours at which the intervention is performed. The "Done" area is also selected which, when entered, will cause step 116 to be performed and the updated information to be entered during step 118.

Since at this time all of the interventions for problem No. 1 have been dealt with, the user selects "Done" for a second time, step 122, indicating that there are no more interventions. The operation then proceeds either to step 2.2 to select a new problem or to step 2.6A with the user selecting a "Done" key for a third time to indicate that there are no further problems to be charted on. If the operation returns to step 2.2, the display would be as shown in FIG. 12 with information generated for problem No. 1 appearing on the left-hand screen, but with a problem category menu such as is shown in FIG. 4 or FIG. 5 on the right display side. After a problem category is selected, the display could be as shown in FIG. 12, a menu of selected problems to be charted on appearing on the right-hand screen.

As previously indicated, operations 2.2–2.6 will be performed for each additional problem until all problems for the patient health plan have been charted on. At this time, the user performs step 2.6A, causing the operation to proceed to step 2.7.

Referring to FIG. 2.7, it is seen that during step 124, the user selects to store the information and during step 126, all of the information including the support data which was generated for the patient during the generation of the patient health plan is stored in a progress note area in a memory of the appropriate host station 32. When step 2.7 is completed, the operation proceeds to step 2.8 to also store all of the patient health plan inforation which has been generated, except for the support data, in the patient health plan area for the patient of the appropriate memory at the host station. When step 2.8 has been completed, the generation of the patient health plan for the particular patient is finished and the user may either proceed to generate a patient health plan for another patient or may perform other functions.

It should at this point be noted that, once generated by the user, the patient health plan may be modified only by the system in response to progress notes or the like. The user cannot directly modify an entered patient health plan.

Progress Note Application:

FIG. 3 is a top view or general flow diagram for the enter progress note application. Referring to this figure, the first step in the progress note application is to enter the progress notes and to decide what type of progress notes will be entered. This is accomplished during step 3.1 by providing to the user a menu of progress note options. Of the available progress note options, only two are of concern with respect to the present invention. The first is to add a new problem. If this option is selected, the operation returns to step 2.2 (FIG. 2.0) to cause a new problem to be selected and entered into the system.

The second option which is of concern is the "Select Active Problem" option. If this option is selected during step 3.2, the system displays the active problems for the patient which are currently in the system and the user selects the problem to be charted on. The operation then proceeds through step 3.3 where the user is given an opportunity to change the etiology for the problem, step 3.4 where the user is given an opportunity to select support data, step 3.5 where the user is given an opportunity to evaluate the progress towards the expected outcomes, step 3.6 where the user may revise the expected outcomes and step 3.7 where the user may revise the interventions. From step 3.7, the process may return to step 3.2 to permit the user to select another active problem on which to chart.

When the user has charted on all active problems of interest, the operation proceeds to step 3.7A where the user selects "Done". During step 3.8, the user selects "Store", causing the revised information on the selected problems to be stored in the progress notes section of a memory at the appropriate host station 32. During step 3.9, the revised information is also stored in a patient health plan section of the host station memory. However, while the current information is stored in the host station memory, the prior information is not destroyed. Therefore, archival records are available on the patient which may, if necessary or desired, be reviewed at a later date for research, evaluation, legal or other purposes.

Figure 13:

FIG. 3.1 is a flow diagram of step 3.1 and FIG. 13 is a screeen display useful in performing this function. The first step in FIG. 3.1, step 130, is to select progress notes from an appropriate master menu, causing a display such as that shown in FIG. 13 to appear on the screen. The window in this display contains a number of progress notes options. In this menu, menu items 132-135 relate to patient assessment/review of systems, narrative notes, a transfer/discharge note, which is done when a patient changes units or the hospital and represents a summary of the patient's stay at the unit or hospital, and a look at the patient's data base, respectively. These progress notes options are not of concern in connection with the present invention. Selection of one of these options is represented by step 136 in FIG. 3.1. Step 138 represents selecting the "Add New Problem" option in the progress notes menu. As previously indicated, if this option is selected, the operation returns to step 2.2 (FIG. 2.0), to add a new problem into the system.

Step 140 represents the selection of the final option, the "Chart Active Problem" option. If this option is selected, the operation proceeds to step 3.2. A flow diagram for step 3.2 is shown in FIG. 3.2. An illustrative screen display for this step is shown in FIG. 14. Referring to FIG. 3.2, during step 142, the system displays an active problem list, which includes all of the problems which were entered into the system during either the generation of the patient health plan or during a prior progress notes step. An example of an active problem list is shown in FIG. 14.

During step 144, the user selects a problem from the active problem list by, for example, using the track ball 48 to highlight a problem as shown in FIG. 14. The system then displays the selected problem.

When step 3.2 has been completed, the operation proceeds to step 3.3 during which the etiology stored during the generation of the patient health plan may be modified. FIG. 3.3 is a flow diagram of this operation. However, since in the example from which the screen displays were generated, it was assumed that no changes in etiology were made, there are no screen displays for this step.

Referring to FIG. 3.3, during step 148, the first step in this operation, the system displays on the right-hand side of the screen the etiologies for the active problem selected. The user may then either select "Done" as was the case for the illustrative example (step 150), which causes the operation to proceed to step 3.4, select to delete an etiology, step 152, or select to add an etiology, step 154. If the user elects to delete an etiology, the operation proceeds to step 154, during which the current etiologies are again displayed, and to step 156 where the user selects the one or more etiologies to be deleted. The user then selects "Done" during step 158, resulting in the system displaying the updated selections during step 160, which updated selections in this case would be the prior etiologies without the etiologies which had been deleted. From step 160, the operation returns to step 148, the display of step 160 replacing the initial display of step 148, and the user again having the option to either select "Done" or to delete or add etiologies. If in this instance, the user elects to add an etiology, the operation proceeds from step 154 to step 162 to display etiologies which could potentially be added for the given problem. During step 164, the user selects etiologies either from the display menu or manually entered to be added. When all desired etiologies have been added, the user selects "Done", step 158, and the operation proceeds through steps 160 and 148 This sequence of operations continues until step 150 is performed, causing the operation to proceed to step 3.4.

Figure 17:
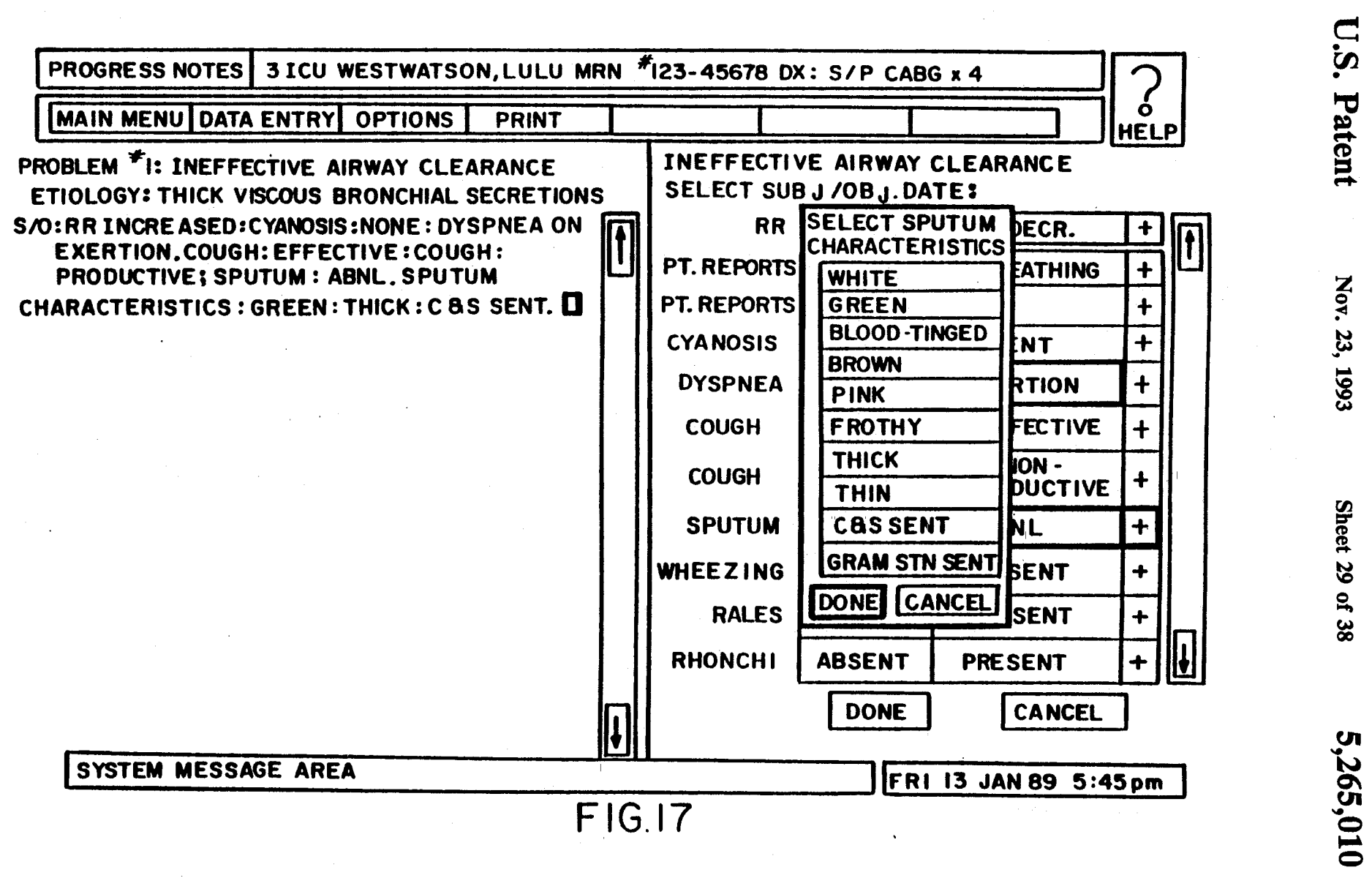

Step 3.4 is flow diagrammed in FIG. 3.4 and screen displays for this step in the operation are shown in FIGS. 15, 16 and 17. The first step in this operation, step 170, is to display a listing of possible supportive data, also referred to as "Subjective/Objective Data" for the selected problem. FIG. 15 shows such a listing being displayed on the right hand side of the screen. During step 172, the user makes selections from the listing of "Subjective/Objective Data" as illustrated on the left-hand side of the screen in FIG. 16. The rightmost column for each item contains a plus sign which, when selected, causes additional options concerning such item to be displayed. For example, in FIG. 16, the plus sign opposite the "Sputum" item has been selected, resulting in the additional display shown in FIG. 17 being provided for selected sputum characteristics. The user selects various characteristics from this window display and then selects "Done", causing the selections to be entered into the system and the original display shown in FIG. 16 to be restored. FIG. 18 shows additional items being selected after the "Sputum" item and also shows the "Done" key being selected (step 174). This causes step 176, the display of the selected supporting data, to occur. This display is also shown in FIG. 18.

When step 3.4 has been completed, the operation proceeds to step 3.5 to evaluate progress toward the desired outcome. FIG. 3.5 is a more detailed flow diagram of this step and FIGS. 19-24 are screen displays useful in performing this operation. During step 180, the first step in this operation, the system displays expected outcomes and due dates and may also identify those requiring evaluation. For example, in FIG. 19, the outcome No. 1 is displayed along with its due date. The menu in FIG. 19 provides a listing of potential outcome statuses. In this figure, the user has selected "Patient Achieving Outcome, but Progress Slower Than Expected". The display of the outcome choices is step 182 and the selection is step 184. Once the user indicates a particular outcome status, the system provides a menu of potential reasons for the indicated status. This is shown in FIG. 20 where the user also indicates two potential reasons why progress has been slower than expected and enters these reasons by selecting "Done". These reasons are also recorded on the left-hand side of the screen as shown in FIG. 20.

At this point, the system determines if an outcome change is required (step 185). For example, for the problem being considered, the outcome has not been met and the due date is the current date. The display of FIG. 21 is, therefore, provided, alerting the user that a change is required. An important feature of the system is that the user is thus forced to make a change at this point, step 187, in order to proceed. The user may modify the expected outcome by changing the expected outcome date to a later date or by returning to step 184 and indicating that the outcome has been met. In FIG. 22, it is seen that the due date has been modified to a date two days later before being accepted and the new date is displayed on the left hand side of the screen.

When all of the above have been completed for the first outcome, the user may move to the next outcome (step 186) and repeat these operations. Thus, in FIG. 23, expected outcome No. 2 is displayed and it is indicated that the patient has met this outcome. This may result in this outcome being deleted from future progress note displays since it is no longer necessary to chart on this outcome. However, an archival record of this outcome, including the date it was achieved, is maintained. This sequence of operations continues until the user has reviewed all expected outcomes.

Figure 24:
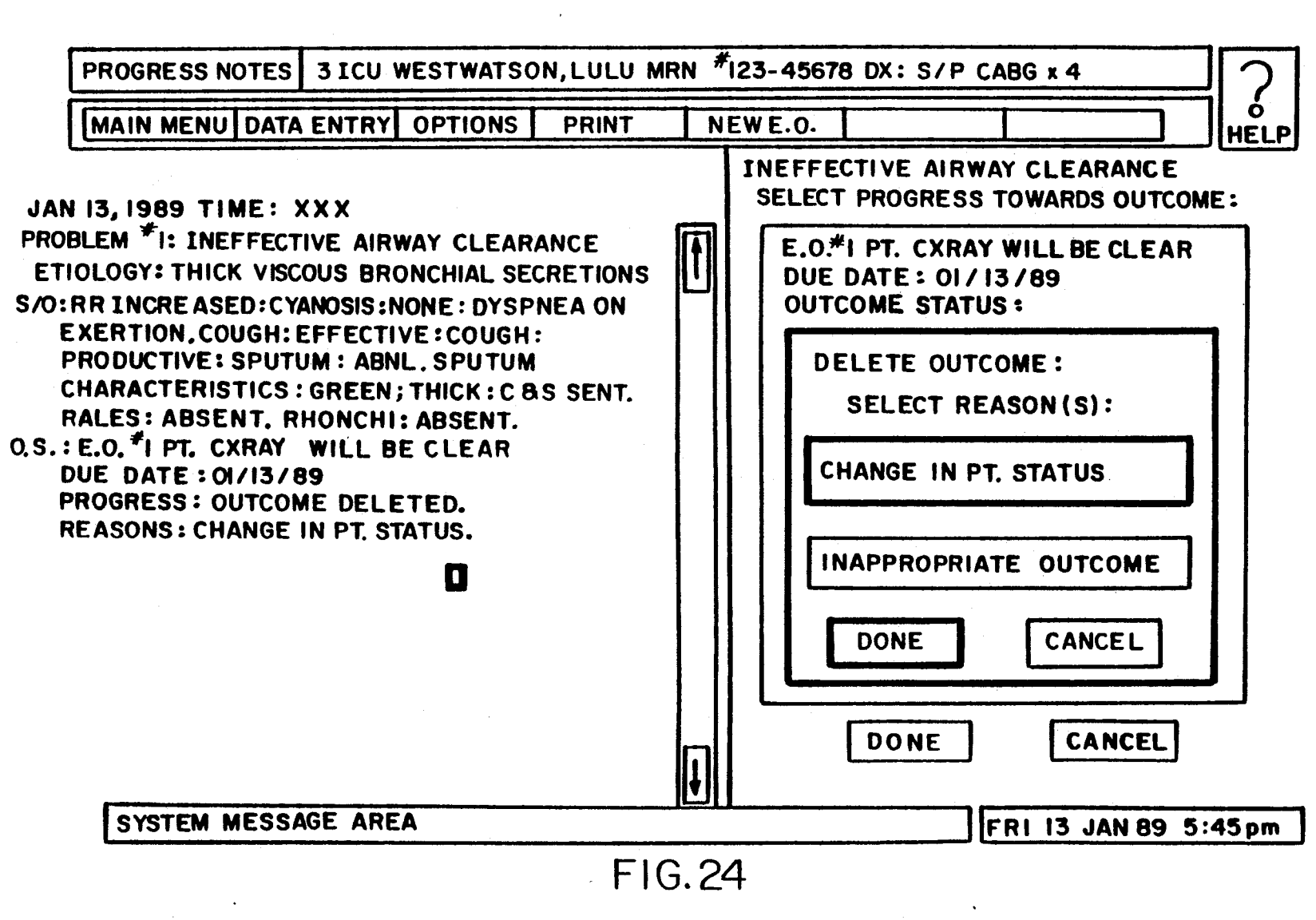

During step 3.6, it is also possible to revise expected outcomes. In the discussion above, this operation was performed during step 3.5, particularly when required because of a failure to achieve an expected outcome. However, it is also possible to perform this as a separate operation. Referring to FIG. 3.6, which is a detailed flow diagram of this operation, it is seen that when an expected outcomes and due dates display is provided, such as that shown in FIG. 19, the user may delete the expected outcome, step 192, may add expected outcomes, step 194, may modify an expected outcome, step 196, or may select "Done", step 198, leaving all the expected outcomes in their current state. If the user selects to delete expected outcomes, the operation proceeds from step 192 to step 200 to display a possible outcome to be deleted. This would be one of the outcomes provided in the system. During step 202 the user selects the outcome to be deleted. During step 204, the system displays the selected outcome for deletion with deletion rationale. This is shown in FIG. 24. In FIG. 24, the user selects as a rationale "Change in Patient Status" (step 206) and during step 208, the user selects "Done", causing the system to delete this outcome from the list of outcomes (step 210). The operation then returns to step 190 to permit other changes in outcome, if desired.

If the user elects to add an expected outcome, the system proceeds from step 194 to step 212 during which the system displays possible additional outcomes which may be added for the give problem. During step 214, the user selects one or more new outcomes to add from the list provided or manually added and then, during step 216, selects "Done". The system then displays the expected outcomes with default due dates as in step 96 (FIG. 2.5). The user may then accept the default due dates or may modify these due dates during step 220, step 220 being performed in the same manner as step 98. When all of the due dates are acceptable, the user selects "Done" (step 222) and the system displays the new current outcomes with the due dates (step 224). From step 224, the operation returns to step 190.

Finally, if from step 190 the user selects to modify an expected outcome, the operation proceeds from step 196 to step 226 to display possible outcomes to be modified. The user selects outcomes to be modified during step 228 and then selects "Done" during step 230. This causes the system to display the selected expected outcomes with due dates, step 232. During step 234, the user may then modify these due dates. When the user has finished modifying due dates, the user selects "Done", step 236, and the operation returns to step 190.

Figure 26:
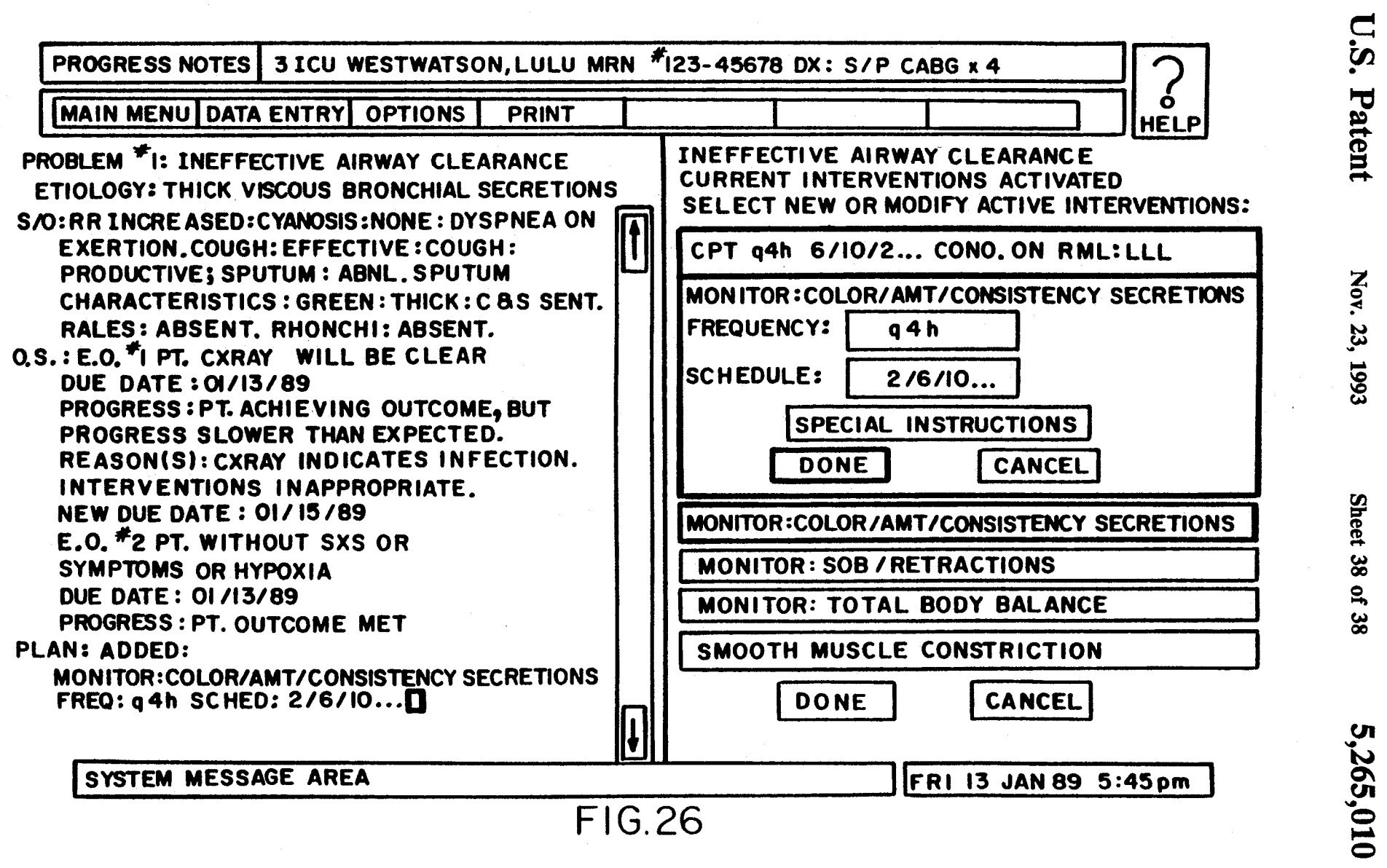

When step 3.6 has been completed, the operation proceeds to step 3.7 to revise interventions. FIG. 3.7 is a flow diagram of step 3.7 and FIGS. 25 and 26 are exemplary displays useful in performing this operation. Step 3 7 begins with the system displaying a current list of interventions along with the frequency schedule and special instructions for each intervention. FIG. 25 shows such a display. From step 240, the operation can proceed to either step 242 to delete an intervention, to step 244 to add an intervention, to step 246 to modify an intervention, or to step 248 to select "Done" which terminates step 3.7. If the user selects step 242, the operation proceeds to step 250 to display possible interventions to be deleted and to step 252 during which the user selects interventions to be deleted. When the user has selected all interventions to be deleted, "Done" is selected during step 254, resulting in the system updating the list of interventions during step 256 to remove the deleted item and then returning to display the current list of interventions, etc. with the deleted intervention removed (step 240).

If the user elects to add an intervention, the operation proceeds from step 244 to step 258 to display a list of possible interventions to be added based on the problem stated. During step 260, the user selects from the list of potential interventions, new interventions which should be added. The user may also write in additional interventions at this point, if desired. When all desired interventions have been selected, the user selects "Done", step 262, and the operation proceeds to step 264 to display the selected interventions with default frequencies, schedules and special instructions. This is equivalent to step 110 (FIG. 2.6). The user may then select or add or modify special instructions during step 266 and/or modify frequency or schedules during step 268. These are equivalent to steps 112 and 114 in FIG. 2.6 and are performed in the same manner. When the displayed special instructions, frequency and schedule are all acceptable, the user selects "Done", step 254, and the system updates the list of interventions with frequency, schedule and special instructions to include the additions (step 256). The operation then returns to step 240 to display the current list of interventions, etc. which will include the added interventions.

If from step 240 the user elects to modify an existing intervention, the operation proceeds from step 246 to step 274 during which the system displays interventions currently in the system which may be modified. This would typically be all of the interventions currently in the system for the selected problem and patient. During step 276, the user selects one or more of the interventions to be modified and then, during step 278, selects "Done". This causes the system to display the selected interventions with the frequency, schedule and special instructions during step 280. One such display is shown in FIG. 26. During step 282, the user then modifies frequency, schedule and/or special instructions as appropriate. When step 282 is completed to the user's satisfaction, the user selects "Done", step 254, and the system updates the list of interventions (step 256) with frequency, schedule and special instructions to reflect the changes made during step 282. The operation then returns to step 240.

As indicated above, step 3.7 is terminated by the user selecting "Done" during step 248. This causes the operation to return to step 3.2 to generate a display such as that shown in FIG. 14, permitting another active problem to be charted on. When, at this stage in the operation, there are no additional problems which the use wishes to chart on, the user selects "Done", step 3.7A and the operation proceeds to perform steps 3.8 and 3.9 to record the updated progress notes in the progress note section and patient health plan section, respectively, of a memory in the appropriate host station 32.

Progress notes are recorded and stored sequentially as generated. However, the fields of the patient health plan are updated t reflect current information while also retaining prior information in the same area. Thus, referring to FIG. 12, the patient health plan shown on the left hand side of the figure would be updated to indicate the due date for expected outcome No. 1, Patient X-ray Will be Clear, to be Jan. 15, 1989, which is the date this outcome was changed to during the generation of progress notes. It would also be indicated that this change was made on Jan. 13, 1989. However, this field would also indicate that the original due date was Jan. 13, 1989, which date was entered on Jan. 10, 1989. Any problems which were deleted would still be stored, but would contain an indication that the problem was deleted and the date or that the outcome had been met and the date.

When a user wanted a display of the patient's health plan, the user would select Display of Patient Health Plan from a master menu and would then be presented with a menu having two options. The first option would be to display the current patient health plan which would include only currently active problems, excluding problems which have been deleted, and only current outcome dates, frequencies, schedules, special instructions and the like. This display would look very much like the display on the left hand side of FIG. 12, with the current information being displayed. The system determines current information by the date stored with each entry.

The second option would be to display a historical patient health plan which would include, in addition to the current items, the previous or original entries and deleted or completed entries. A suitable indication would be provided so that the user could determine outcomes which had been achieved and when achieved, items which have been deleted and when deleted and any other changes. This would permit the health care professional to obtain a comprehensive view of the patient's status and progress during the patient's stay at the facility.

A system for use in a health care facility is thus provided which facilitates the generation of care plans or health plans and of progress notes and of the coordination of the health plan and progress notes so that changes or updates in one are reflected in the other. Archival records in coded, machine-readable form are available from both. The system thus provides for substantially uniform patient records which are easy to generate and update, which facilitate the following of an original health plan, which provides full information on the reasons for deviations from this plan, and which facilitates the generation of archival records or other records required for research, audit or similar purposes. The system also assures that outcomes ar reviewed and that they are modified if not met.

While the invention has been particularly described above with reference to a preferred embodiment, it is apparent that the particular sequence of operations both in the generation of the patient health plan and in the generation of the progress notes is for purposes of illustration only and that the various operations could be performed in other sequences, that certain of the operations could be eliminated or other operations added as required at a particular health care facility and that different formats might be used for all of the screen displays. The systems configuration shown in FIG. 1 is also for purposes of illustration and other systems configurations are also possible while still staying within the scope of the invention.

Thus, while the invention has been particularly shown and described above with reference to the preferred embodiment, the foregoing and other changes in form and detail may be made therein by one skilled in the art without departing from the spirit and scope of the invention.

What is claimed is:

1. A documentation system for a hospital patient comprising:
    means for generating an initial health care plan for the patient, the care plan having a plurality of entries, including entries identifying patient's health care problems, expected outcomes for such problems, and interventions to achieve such outcomes;
    means for periodically entering progress notes on the patient into the system, said progress notes including, as appropriate, changes for one or more entries of the care plan; and
    means responsive to a change being entered for an entry in a progress note for automatically updating the care plan for the patient by making a corresponding change in the corresponding care plan entry.

2. The system as claimed in claim 1 including means for storing the initial care plan and all updates thereof, whereby an audit trail of patient care and progress is maintained.

3. The system as claimed in claim 1 including a display means; and
    wherein said means for generating includes means for displaying an initial menu on said display means, means for indicating selections from the menu, and means responsive to each menu selection for displaying a subsequent menu until the care plan is completed.

4. The system as claimed in claim 3 wherein each menu item is coded; and including means for searching the system for entries having a selected code.

5. The system as claimed in claim 3 wherein a user may make additions to at least selected ones of said menus.

6. The system as claimed in claim 3 wherein a user may make alterations in at least selected ones of said menus.

7. The system as claimed in claim 3 wherein the initial menu includes an indication of problem categories.

8. The system as claimed in claim 3 wherein a problem category may be chosen from a selected menu, and including means responsive to said problem category for displaying a menu of preselected potential problems associated with the category.

9. The system as claimed in claim 8 including means responsive to the selection of a potential problem from a menu for displaying a menu of selected outcomes.

10. The system as claimed in claim 9 including means responsive to the user indicating a selected outcome for displaying outcome due dates.

11. The system as claimed in claim 10 including means for permitting the user to change an outcome due date.

12. The system as claimed in claim 9 including means responsive to a selected outcome for displaying a menu of selected interventions, and means for selecting one or more of the interventions.

13. The system as claimed in claim 12 including means responsive to each intervention selected for displaying frequency and schedule for such intervention.

14. The system as claimed in claim 13 including means for providing special instructions for each intervention.

15. The system as claimed in claim 8 wherein said menus of problem categories contain potential diagnosis.

16. The system as claimed in claim 8 including means responsive to the selection of a potential problem for displaying a menu of etiologies for such problem; and
means for selecting one or more etiologies from said menu.

17. The system as claimed in claim 8 including means responsive to the selection of a potential problem for displaying a menu of selected support data; and
means for selecting support data appropriate to the patient from said menu.

18. The system as claimed in claim 3 wherein standards are established and indicated for selected ones of said menus; and
including means for facilitating the selection of the indicated standard from the menu.

19. The system as claimed in claim 3 including means for storing a running record of all selections made from said menus, said running record representing the care plan.

20. The system as claimed in claim 19 wherein said display means has a split screen, means for displaying said menus on one side of the split screen, and means for displaying said stored running record on the other side of the split screen.

21. The system as claimed in claim 1 including means operative when a system user indicates a desire to enter a progress note for providing a menu of progress note options.

22. The system as claimed in claim 21 wherein one of said progress note options is to chart on an active problem, and means responsive to the selection of the chart on an active problem option for displaying a menu of active problems for the patient.

23. The system as claimed in claim 22 including means responsive to the selection of an active problem to chart on for displaying a menu relative to said problem, and means responsive to an indication that action from a displayed menu is complete for displaying a successive menu.

24. The system as claimed in claim 23 wherein said display is a split screen display, and including means for displaying a menu on one side of the split screen and user selections from the menu on the other side.

25. The system as claimed in claim 23 wherein items displayed in conjunction with a given menu may be deleted or modified or new items may be added.

26. The system as claimed in claim 25 including means for requesting a display of additional information relating to a menu item, and means for selecting or modifying said additional information.

27. The system as claimed in claim 25 including means responsive to the completion of action on a given menu for displaying information concerning one or more items on said menu, and means for performing selected actions on said additional information.

28. The system as claimed in claim 23 wherein said menus may include menus for the selected active problem for one or more of etiologies, signs and symptoms, expected outcomes, progress toward expected outcomes and interventions.

29. The system as claimed in claim 23 wherein expected outcomes for the selected active problem are in the system; and wherein one of the displayed menus is a list of potential progress toward the expected outcome.

30. The system as claimed in claim 29 including means responsive to the selection of a potential outcome for displaying a menu of reasons for the outcome, and means for the selection of one or more of said reasons.

31. The system as claimed in claim 30 wherein at least selected ones of said menus are user configurable.

32. The system as claimed in claim 23 wherein one of said menus is of expected outcomes with outcome due dates; including
means responsive to an outcome not being achieved on the due date for inhibiting the entering of the progress note until an appropriate change is made in the due date or outcome.

33. A method for performing hospital documentation comprising the steps of:
generating an initial health care plan for a patient, the care plan having a plurality of entries including entries identifying patient medical problems, expected outcomes for such problems and medical interventions to achieve the outcomes;
periodically entering progress notes on the patient, said progress notes including, as appropriate, changes for one or more entries of the care plan; and
automatically updating the care plan for the patient in response to a change being entered for an entry in a progress note by making a corresponding change in the corresponding care plan entry.

34. The method as claimed in claim 33 including the step of storing the initial care plan and all updates thereto, whereby an audit trail of patient care and progress is maintained.

35. The method as claimed in claim 33 wherein the step of generating a care plan includes the steps of displaying an initial menu, indicating selections from menus, displaying a subsequent menu in response to each menu selection, and repeating the display of subsequent menus and the selection from such menus until the care plan is completed.

36. The method as claimed in claim 35 including the step of coding each menu item, and searching the system for entries having a selecting code.

37. The method as claimed in claim 35 including the step of making additions to at least selected ones of said menus.

38. The method as claimed in claim 35 including the step of making alterations in at least selected ones of said menus.

39. The method as claimed in claim 35 including the step of displaying an initial menu having an indication of problem categories.

40. The method as claimed in claim 35 including the steps of indicating a problem category form a selected menu, and displaying a menu of preselected potential problems associated with a particular problem category in response to the selection of such category.

41. The method as claimed in claim 40 including the steps of displaying a menu of selected outcomes in response to the selection of a potential problem.

42. The method as claimed in claim 41 including the step of displaying outcome due dates in response to the user indicating a selected outcome.

43. The method as claimed in claim 42 including the step of changing an outcome due date in response to a user input.

44. The method as claimed in claim 41 including the steps of displaying a menu of selected interventions in response to a selected outcome, and selecting one or more of said interventions.

45. The method as claimed in claim 44 including the step of displaying frequency and schedule for each intervention in response to the selection thereof.

46. The method as claimed in claim 45 including the step of providing special instructions for each intervention.

47. The method as claimed in claim 40 wherein said menus of problem categories contain potential diagnosis.

48. The method as claimed in claim 40 including the steps of displaying a menu of etiologies for a potential problem in response to the selection of such problem, and of selecting one or more etiologies from said menu.

49. The method as claimed in claim 40 including the steps of displaying a menu of selected support data in response to the selection of a potential problem, and selecting support data appropriate to the patient from said menu.

50. The method as claimed in claim 35 wherein standards are established and indicated for selected ones of said menus; and
   including the step of facilitating the selection of the indicated standard from the menu.

51. The method as claimed in claim 35 including the step of storing a running record of all menu selections, said running record representing the care plan.

52. The method as claimed in claim 51 including the steps of displaying menus on one side of a split screen and displaying the stored running record on the other side of the split screen.

53. The method as claimed in claim 33 including the step of providing a menu of progress note options in response to an indication from a system user of a desire to enter progress notes.

54. The method as claimed in claim 53 wherein one of said progress note options is to chart on an active problem; and including the step of displaying a menu of active problems for the patient in response to the selection of the chart on an active problem option.

55. The method as claimed in claim 54 including the steps of displaying in response to the selection of an active problem to chart on, a menu relevant to said problem, and displaying a successive menu in response to an indication that action from a current menu is complete.

56. The method as claimed in claim 55 including the steps of displaying a menu on one side of a split screen display, and displaying user selections form the menu on the other side of the split screen display.

57. The method as claimed in claim 55 wherein items displayed in conjunction with a given menu may be deleted or modified, or new items may be added.

58. The method as claimed in claim 57 including the steps of requesting a display of additional information relating to a menu item, and selecting or modifying said additional information.

59. The method as claimed in claim 57 including the steps of displaying additional information concerning one or more items on a given menu in response to the completion of action on the given menu, and performing selected action on said additional information.

60. The method as claimed in claim 55 wherein said menus may include menus for the selected active problem, for one or more of etiologies, signs and symptoms, expected outcomes, progress toward expected outcomes and interventions.

61. The method as claimed in claim 55 wherein expected outcomes for the selected active problem are in the system; and wherein one of the displayed menus is a list of potential progress toward an expected outcome.

62. The method as claimed in claim 61 including displaying a menu of reasons for a potential outcome in response to the selection of such outcome, and selecting one or more of said reasons.

63. The method as claimed in claim 35 wherein at least selected ones of said menus are user configurable.

64. The method as claimed in claim 57 wherein one of said menus is of expected outcomes with outcome due dates; and including the step, operative when an outcome is not achieved on the due date, of inhibiting the entering of the progress note until an appropriate change is made in the due date or outcome.

65. A documentation system for a hospital patient comprising:
   means for generating an initial health care plan for the patient, the care plan identifying patient health care problems, expected outcomes for such problems, due dates for each expected outcome and interventions to achieve such outcomes;
   means for periodically entering progress notes on the patient into the system; and
   means responsive to an outcome not being achieved on the due date for inhibiting the entering of the progress note until an appropriate change is made in the due date or outcome.

* * * * *